(12) United States Patent
Botti et al.

(10) Patent No.: US 9,533,048 B2
(45) Date of Patent: Jan. 3, 2017

(54) MUCOSAL DELIVERY OF DRUGS

(75) Inventors: Paolo Botti, Vessy/Geneva (CH); Sylvie Tchertchian, Monnetier-Mornex (FR)

(73) Assignee: ARISGEN SA, Plan-les-Ouates (CH)

( * ) Notice: Subject to any disclaimer, the term of this patent is extended or adjusted under 35 U.S.C. 154(b) by 0 days.

(21) Appl. No.: 14/122,182

(22) PCT Filed: May 25, 2012

(86) PCT No.: PCT/EP2012/059890
§ 371 (c)(1),
(2), (4) Date: Feb. 18, 2014

(87) PCT Pub. No.: WO2012/160203
PCT Pub. Date: Nov. 29, 2012

(65) Prior Publication Data
US 2014/0187489 A1    Jul. 3, 2014

(30) Foreign Application Priority Data
May 25, 2011   (EP) .................................... 11004319

(51) Int. Cl.

| | | |
|---|---|---|
| A61K 38/26 | (2006.01) | |
| A61P 3/10 | (2006.01) | |
| A61P 7/12 | (2006.01) | |
| C07K 14/605 | (2006.01) | |
| A61K 47/22 | (2006.01) | |
| A61K 9/00 | (2006.01) | |
| A61K 47/14 | (2006.01) | |
| A61K 47/24 | (2006.01) | |
| A61K 47/28 | (2006.01) | |
| A61K 38/11 | (2006.01) | |
| A61K 38/22 | (2006.01) | |
| A61K 38/23 | (2006.01) | |
| A61K 38/28 | (2006.01) | |
| A61K 38/29 | (2006.01) | |

(52) U.S. Cl.
CPC ............ *A61K 47/22* (2013.01); *A61K 9/0014* (2013.01); *A61K 38/11* (2013.01); *A61K 38/2278* (2013.01); *A61K 38/23* (2013.01); *A61K 38/26* (2013.01); *A61K 38/28* (2013.01); *A61K 38/29* (2013.01); *A61K 47/14* (2013.01); *A61K 47/24* (2013.01); *A61K 47/28* (2013.01)

(58) Field of Classification Search
CPC .... A61K 38/11; A61K 38/2278; A61K 38/23; A61K 38/26; A61K 38/28; A61K 38/29; A61K 47/14; A61K 47/22; A61K 47/24; A61K 47/28; A61K 9/0014
See application file for complete search history.

(56) References Cited

U.S. PATENT DOCUMENTS

| | | | |
|---|---|---|---|
| 4,874,795 A * | 10/1989 | Yesair ........................... 514/725 | |
| 5,863,555 A | 1/1999 | Heiber et al. | |
| 6,191,105 B1 * | 2/2001 | Ekwuribe ............ A61K 9/1075 | 424/400 |
| 6,245,349 B1 * | 6/2001 | Yiv ...................... A61K 9/1075 | 424/400 |
| 6,248,363 B1 * | 6/2001 | Patel et al. ..................... 424/497 | |
| 8,624,044 B2 * | 1/2014 | Botti .................... C07D 323/00 | 549/352 |
| 2003/0027833 A1 | 2/2003 | Cleary et al. | |
| 2003/0171259 A1 | 9/2003 | Modi | |
| 2005/0025820 A1 * | 2/2005 | Kester et al. ................. 424/450 | |
| 2005/0042271 A1 * | 2/2005 | Xiong .................. A61K 9/7053 | 424/449 |
| 2012/0302502 A1 * | 11/2012 | Botti ..................... A61K 9/006 | 514/11.7 |
| 2015/0031631 A1 | 1/2015 | Mamluk et al. | |

FOREIGN PATENT DOCUMENTS

| | | | | |
|---|---|---|---|---|
| EP | 0465 423 | * | 1/1992 | ............ A61K 31/19 |
| EP | 1 905 454 | | 4/2008 | |
| JP | 1-175943 | | 7/1989 | |
| JP | 4-338311 | | 11/1992 | |
| JP | 2010-120873 | | 6/2010 | |
| JP | 2012-502973 | | 2/2012 | |
| JP | 2012-106992 | | 6/2012 | |
| WO | WO-2009/075258 | | 6/2009 | |

OTHER PUBLICATIONS

Flynn et al. Cholesterol Solubility in Organic Solvents. J Pharmaceutical Sciences, 1979. vol. 68, No. 9, pp. 1090-1097.*
Scholfield. Composition of Soybean Lecithin. J American Oil Chemists' Society. 1981, vol. 58, No. 10, pp. 889-892.*
Genaro Alfonso R.: "Remington, The science and practice of pharmacy", 2000, Lippincott Williams & Wilkins, XP002657559, pp. 922-923.
Williams Adrian C., et al.: "Penetration enhancers", Advanced Drug Delivery Reviews, Elsevier BV, Amsterdam, NL, vol. 56, No. 5, Mar. 27, 2004, pp. 603-618, XP002463042.
Veuillez F et al.,: "Factors and strategies for improving local absorption of peptides", European Journal of Pharmaceutics and Biopharmaceutics, Elsevier Science Publishers B.V., Amsterdam, NL, vol. 51, No. 2, Mar. 1, 2001, pp. 93-109, XP004257246.
Chun-Ying Cui et al., : "Sublingual delivery of insulin: effects of enhancers on the mucosal lipid fluidity and protein conformation, transport, and in vivo hypoglycemic activity", Biological & Pharmaceutical Bulletin, vol. 28, No. 12, Dec. 1, 2005, pp. 2279-2288, XP055005519.
Hussain A. et al., : "Absorption enhancers in pulmonary protein delivery", Journal of Controlled Release, Elsevier, Amsterdam, NL, vol. 94, No. 1, Jan. 8, 2004, pp. 15-24, XP004480734.

* cited by examiner

*Primary Examiner* — Marcela M Cordero Garcia
(74) *Attorney, Agent, or Firm* — Norris McLaughlin & Marcus, P.A.

(57) ABSTRACT

The present invention provides a composition comprising or consisting of components (a) (i) at least one mono-alkanoyl glycerol ester, wherein alkanoyl is selected from $C_4$ to $C_{21}$ alkanoyl, preferably from octanoyl and decanoyl; and (b) (i) at least one compound selected from cholesterol, phosphatidyl cholines and phosphatidyl glycerols, wherein the acyl moieties of the phosphatidyl moieties are independently selected from $C_6$ to $C_{21}$ alkanoyl and $C_6$ to $C_{21}$ alkenoyl.

16 Claims, 3 Drawing Sheets

Nonactin

Esaglycine cyclic peptide

Poly(cyclic)Glycolic ester

Poly(cyclic)Lactic ester

Oxo Crown ethers

MUCOSAL DELIVERY OF DRUGS

BACKGROUND OF THE INVENTION

This invention relates to a composition comprising or consisting of components (a) (i) at least one mono-alkanoyl glycerol ester, wherein alkanoyl is selected from $C_4$ to $C_{21}$ alkanoyl, preferably from octanoyl and decanoyl; and (b) (i) at least one compound selected from cholesterol, phosphatidyl cholines and phosphatidyl glycerols, wherein the acyl moieties of the phosphatidyl moieties are independently selected from $C_6$ to $C_{21}$ alkanoyl and $C_6$ to $C_{21}$ alkenoyl.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Peptide-based drugs are typically delivered by injection, since oral delivery by ingestion is often hindered by poor intrinsic permeability and degradation in the gastrointestinal (GI) tract. Nevertheless, the potential therapeutic benefit or oral delivery remains significant, including ease of use and better overall patient compliance.

Mucosal delivery of peptides into the blood stream of a host across various mucosal membranes, such as found in the GI tract, lung, nasal cavity and oral cavity, is possible for a number of peptides and peptide formulations. However, the fraction of an administered dose of unchanged peptide that reaches the systemic circulation (i.e., bioavailability) normally varies depending on the particular route of delivery, peptide and formulation. Thus, the non-invasive delivery of peptide drugs by mucosal routes offers significant flexibility.

For example, delivery of drugs via oral mucosa provides direct access to the systemic circulation through the internal jugular vein, allowing them to bypass the gut and hepatic first-pass metabolism, and enter the bloodstream for rapid on-set of effect. As such, the mucosal lining in the oral cavity represents a promising topical route for the delivery of large therapeutic molecules such as insulin, interferons, and interleukins (Veuillez et al., Eur. J. Pharm. Biopharm. (2001)51: 93-109; and Sudhakar et al., J. Control. Release (2006) 114:15-40; and Amin et al., Drug Delivery Technology (2007) 7(3) 48, 50-55).

One drawback of oral mucosal delivery of larger molecules is their poor overall bioavailability. In this regard, various approaches have been explored to improve the oral mucosal absorption of peptides, including use of absorption enhancers to increase mucosal membrane permeability and/or the addition of enzyme inhibitors to increase drug stability. Many substances can function as absorption enhancers, one of the most popular being detergents such as bile acid salts, sodium lauryl sulfate, and the like based on intercellular lipid solubilization (Aungst et al., Intl. J. Pharmaceutics (1989) 53(3); 227-35; Druker, D. J., Curr Pharm Design (2001) 7(14):1399-1412; and Berstein, G., Drug Development Res. (2008) 67(7):597-599). Cyclic compounds such as crowns have also been used (WO 08/037,484).

Reservoir-type devices filled with drug, along with cholate as a penetration enhancer, have been reported for buccal delivery of insulin (U.S. Pat. Nos. 4,671,953; 4,863, 737; 5122127; and 5,132,114). Lipid vesicles composed of soybean phosphatidylcholine, cholesterol, and sodium deoxycholate, has been reported to enhance insulin bioavailability as well (Yang et al., Chem. Pharm. Bull. (2002) 50:749-753). Gels composed of Pluronic F-127 (PF-127) containing insulin and unsaturated fatty acids, such as oleic acid (18:1), eicosapentaenoic acid (20:5), or docosahexaenoic acid (22:6) have been reported (Morishita et al., Int. J. Pharm. (2001) 212:289-293). The absorption enhancer lysalbinic acid, which is a product of the alkaline hydrolysis of egg albumin and a mild detergent, also has been reported for molecules such as α-interferon and insulin (Starokadomskyy et al., Int. J. Pharm. (2006) 308:149-154). Various delivery systems have been reported for buccal delivery of glucagon-like insulinotropic peptide (GLP-1) (U.S. Pat. Nos. 5,863,555 and 5,766,620).

A variety of mucoadhesive dosage forms also have been reported to increase resident time of the delivery system in the oral cavity (Ishida et al., Chem. Pharm. Bull. (1981) 29:810-816; and Senel et al., Curr. Pharm. Biotechnol. (2001) 2:175-186), including, for example, pelleted mucoadhesive polymeric nanoparticles (Venugopalan et al., Pharmazie (2001) 56:217-219), and mucoadhesive tablets (Hosny et al., Boll. Chim. Farm. (2002) 141:210-217).

Mucosal dosage forms employing various solvents have also been reported, such as insulin with soybean lecithin and propanediol (Xu et al., Pharmacol. Res. (2002) 46:459-467), and buccal aerosol sprays and capsules using non-polar solvent (U.S. Pat. No. 5,955,098). Pulmonary delivery formulations of a solution or suspension of various organic solvents have been reported, for example, where the solvent is a class 3 residual solvent such as ethanol, acetone, ethyl acetate, tetrahydrofuran, ethyl ether, and propanol (U.S. Pat. No. 6,680,715).

Despite advances, mucosal delivery systems often include absorption enhancing formulations that exhibit side effects, such as causing irritation of the various mucosal linings in the mouth or airways. Another problem is the repugnant taste of many compositions, particularly for bile salts, pointing to likely issues with patient acceptance and compliance. A different issue relates to the volume required for delivering a sufficient amount of an active peptide ingredient for biological effect, storage stability, and reproducibility.

Various peptides, uses, formulations and delivery routes and systems are reported in the following; U.S. Pat. Nos. 4,671,953; 4,863,737; 5,122,127; 5,132,114; 5,348,701; 5,424,286; 5,545,618; 5,614,492; 5,631,224; 5,766,620; 5,869,082; 6,268,343; 6,312,665; 6,375,975; 6,436,367; 6,451,286; 6,458,924; 6,660,715; 6,676,931; 6,770,625; 6,867,183; 6,902,744; 6,969,508; 6,977,070; 6,998,110; 7,030,082; 7,070,799; 7,169,410; 7,196,059; and International Patent Application Nos.: WO 9715297; WO/1999/ 016417; WO/2002/064115; WO/2003/024425; WO/2004/ 105790; WO/2006/025882; WO/2006/037811; WO/2006/ 103657; WO/2006/105615; WO/2006/127361; WO/2006/ 135930; WO/2007/014391; WO/2007/065156; WO/2007/ 067964; WO/2007/083146; WO/2007/121256; WO/2007/ 146448; WO/2008/037484; WO/2008/145728; WO/2008/ 145732; and WO/2008/016729.

Various references discuss alternatives to subcutaneous injection (s.c.) of peptides and uses, including peroral, intra oral (buccal/sublingual), rectal, transdermal, intra nasal, and intra pulmonary delivery routes: Touitou, E., J. Controlled Rel (1992) 27:139-144; Amin et al., Drug Delivery Technology (2007) 7(3) 48, 50-55; Aungst et al., Pharmaceutical Research (1988) 5(5):305-308; Aungst et al., Intl. J. Pharmaceutics (1989) 53(3):22735; Berstein, G., Drug Development Res. (2006) 67(7):597-599; Druker, D. J., Curr Pharm Design (2001) 7(14):1399-1412; Hosny et al., Bollettino Chimico Farmaceutico (2002), 747(3):210-217; Khafagy et al., *Advanced Drug Delivery Reviews* (2007) 59(15): 1521-1546; Lassmann-Vague et al., *Diabetes & Metabolism* (2006) 32(5, Pt 2):513-522; Morishita et al., *Intl. J. Pharmaceutics* (2001) 212(2):289-293; Patel et al. *Drug Delivery Technology* (2006) 6(3)48-60; Pillion et al., *J. Pharm. Sci.* (1995) 84(11):1276-1279; Portero et al., *Carbohydrate Polymers* (2007) 68(4):617-625; Pozzilli et al., *Metabolism, Clinical and Experimental* (2005) 54(7):930-934; Owens, D. R., *Nature Reviews Drug Discovery* (2002) 1(7):529-540; Rossi et al., *American J. Drug Delivery* (2005) 3(4):215225; Sadrzadeh et al., *J. Pharm Sci* (2007) 96(8): 1925-1954; Starokadomskyy et al., *Intl. J. Pharmaceutics* (2008) 308 (1-2):149-154; Xu et al., *Pharmacological Research* (2002) 46(5:459-487; Yang et al., *S.T.P. Pharm. Sciences* (2001) 11(6):415-419; Yang et al., *Chemical & Pharmaceutical Bulletin* (2002) 50(6):749-753; Klibanov et al. (1995 supra) reported on lyophilization of various biomolecules from aqueous solutions of different pH's and their subsequent solubility in methanol and ethanol.

US 2006/0178304 discloses lyophilization of various glucagon-like peptides from aqueous solutions or suspensions of different phi's and their subsequent solubility in aqueous solutions or suspensions.

SUMMARY OF THE INVENTION

The deficiencies discussed above point to an unmet need for compositions and methods for administering drugs, in particular peptides and polypeptides, the compositions and methods, respectively, being stable, well tolerated, providing enhanced and reliable mucosal delivery, particularly oral mucosal delivery, and being suitable for treatment of diseases and other adverse conditions in mammalian subjects. A related need exists for methods and compositions that provide efficient delivery of larger drugs such as peptides and polypeptides via one or more mucosal and/or dermal routes in therapeutic amounts, which preferably are fast acting, easily administered, have limited adverse side effects such as mucosal irritation or tissue damage, and are reproducible. There is also a need for non-aqueous pharmaceutical and diagnostic compositions of peptides which have improved stability. An additional need relates to the manufacture of such materials, and compositions for the same. The present invention addresses these and other needs.

Accordingly, the present invention provides in a first aspect a composition comprising or consisting of components (a) (i) at least one mono-alkanoyl glycerol ester, wherein alkanoyl is selected from $C_4$ to $C_{21}$ alkanoyl, preferably from octanoyl and decanoyl; and (b) (i) at least one compound selected from cholesterol, phosphatidyl cholines, lysophosphatidylcholines and phosphatidyl glycerols, wherein the acyl moieties of the phosphatidyl moieties are independently selected from $C_6$ to $C_2$ alkanoyl and $C_6$ to $C_{21}$ alkenoyl.

Generally speaking, compositions according to the present invention comprise or consist of various components. Typically, these components are designated (a), (b) and so forth. Each of these components in turn may comprise or consist of one or more constituents or parts which are generally designated (i), (ii) and so forth. Said constituents or parts in turn may either be single compounds or mixtures of more than one compound. Accordingly, when the main embodiment refers to a component (a) (i), it is understood that the main embodiment requires presence of (the) compound(s) defined in part (a) (i). It is furthermore understood that component (a), in preferred embodiments, may comprise a further compound or further compounds, such further compounds being defined, for example, as part (ii) of component (a). In such a case, component (a) may either consist of parts (i) and (ii), or may comprise further compounds in addition to parts (i) and (ii).

Part (i) of component (a) requires at least one, preferably exactly one mono-alkanoyl glycerol ester. Glycerol has three hydroxyl groups, only one of which is esterified with the recited alkanoyl moiety. Preferably, the hydroxyl group in position 1 of glycerol is esterified. The recited $C_4$ to $C_{21}$ alkanoyl moieties may be branched or unbranched, wherein preference is given to unbranched, i.e. n-alkanoyl. In a further preferred embodiment, component (a) or part (i) of component (a) comprises or consists of two mono-alkanoyl glycerol esters. Preferred are $C_6$ to $C_{12}$, in particular $C_8$ to $C_{10}$ alkanoyl moieties including n-octanoyl glycerol, n-nonanoyl glycerol and n-decanoyl glycerol. Preferably, at least one of these two mono-alkanoyl glycerol esters is octanoyl glycerol or decanoyl glycerol. In a further preferred embodiment, component (a) or part (i) of component (a) consists of mono-decanoyl glycerol ester and mono-octanoyl glycerol ester (herein also referred to as octanoyl glycerol and decanoyl glycerol, respectively), preferably in the same amounts. In these two compounds, position 1 of glycerol is esterified. Generally, the mono-alkanoyl glycerol esters are also referred to as acylglycerols herein. Preferably, octanoyl is n-octanoyl and decanoyl is n-decanoyl. Further preferred alkanoyl moieties are disclosed herein below in relation to component (b) (i) which disclosure applies for alkanoyl moieties as comprised in component (a) (i) as well.

Depending on a given route of administration and dosage form, at least one acylglycerol may be included in an amount so that said composition and/or the pharmaceutical or diagnostic composition defined further below is liquid, gel, or a solid or semi-solid at a desired temperature. A solid oral delivery formulation, for example, may employ one or more particular acylglycerols in an amount such that the compositions are solid or semi-solid at temperature of up to about 50° C. to about 55° C. Conversely, a composition can be selected that is a liquid or gel at lower temperatures than this. For instance, a composition can be selected such that at least one acylglycerol is included in an amount to provide a composition that is solid at 4° C., and melts at room temperature, or at or around the temperature of the host, e.g., solid at 4° C. and is melted or begins melting around 37° C.-45° C. Of specific interest is a composition that is a solid or semi-solid at temperatures less than about the body temperature of the host, such as a composition that is a solid or semi-solid at less than about 37° C.-45° C. In general, an acylglycerol with such features (in addition to other components of a given composition) can be chosen based on its melting temperature. Of particular interest are acylglycerols that are solids or semi-solids at ambient room temperature and having a melting temperature of about 60° C. or less, usually about 55° C. or less, and more typically about 53° C. or less, e.g., mono-decanoyl-glycerol, has a melting point of about 53° C. Many such acylglycerols are known and commercially available.

Part (i) of component (b) requires at least one, preferably two and most preferably all three of the recited compounds; see also further preferred embodiments described herein below. Preferably, component (b) consists of part (i) thereof. As is known in the art, the "phosphatidyl" refers to the acyl form of phosphatidic acid, the term "phosphatidic acid" designating a class of compounds which are 1,2-di-acyl-glycerol-3-phosphates. In the recited phosphatidyl cholines and phosphatidyl glycerols, positions 1 and 2 of glycerol as comprised in the phosphatidyl moiety are esterified with acids, which acids give rise to the presence of two acyl moieties in a given phosphatidyl moiety. Accordingly, position 3 of glycerol as comprised in the phosphatidyl moiety bears the phosphate group. Said phosphate group in turn is esterified with choline in case of the recited phosphatidyl cholines and with a second glycerol moiety in case of the recited phosphatidyl glycerols. Lysophosphatidylcholines (lysolecithins) are monoacylglycerolphosphates resulting from partial hydrolysis of phosphatidylcholines. As is known in the art, hydrolysis leads to removal of one of the fatty acid groups.

Part (i) of component (b), to the extent two of the recited compounds are required, may consist of: (1) a phosphatidyl choline and a phosphatidyl glycerol, each of them being as defined above, or (2) a phosphatidyl choline and cholesterol, or (3) phosphatidyl glycerol and cholesterol, or (4) a phosphatidyl choline, or (5) a lysophosphatidylcholine, each of (1) to (5) being a preferred option for (b) (i).

Each occurrence of acyl is independently selected from the recited alkanoyl and alkenoyl moieties. The term "alkenoyl" embraces also polyunsaturated acyl moieties. Polyunsaturated alkenoyl includes alkenoyl with two, three or four carbon-carbon double bonds. This applies throughout the present application. The terms "alkanoyl" and "alkenoyl" refer to branched and unbranched moieties, unbranched alkanoyl and alkenoyl, respectively, being preferred throughout, in either case, preference is given to $C_{10}$ to $C_{18}$ moieties. Preferred alkanoyl moieties are myristoyl (n-tetradeacyl), lauroyl (n-dodecanoyl) and stearoyl (n-octadecanoyl). Preferred, alkenoyl is oleoyl (9Z-octadec-9-enoyl). Also, it is preferred that both acyl moieties within a given compound are identical. Preferred embodiments of di-alkanoyl phosphatidyl glycerols and di-alkanoyl phosphatidyl cholines are the respective di-myristoyl, di-lauroyl and di-stearoyl compounds. Preferred embodiments of di-alkenoyl phosphatidyl glycerols and di-alkenoyl phosphatidyl cholines are the respective di-oleoyl compounds.

The composition according to the first aspect of the invention comprises or consists of at least two components, each component comprising or consisting of at least one compound as specified. This composition is a pre-mixed composition to be used in the formulation of pharmaceutically or diagnostically active agents, in particular of peptides or polypeptides. In case any one of the components of a composition according to the invention (in case of the composition according to the first aspect these are components (a) and (b)) comprises or consists of more than one compound, it is understood that preferably each of the components is provided in pre-mixed form as well prior to combining the components to eventually give rise to the respective composition.

As will be described in more detail below in relation to the pharmaceutical composition of the invention and the methods of preparing said pharmaceutical composition, the pre-mixed composition according to the first aspect may be combined with a pharmaceutically or diagnostically active agent, said agent being dissolved or suspended in an organic solvent. The present inventors discovered that, by using a composition according to the first aspect of the invention, the delivery properties of an active agent, in particular of a peptide or polypeptide, can be significantly enhanced, in particular, the delivery across a mucosa, preferably the oral mucosa is enhanced or rendered possible at all. Similarly, also dermal and transdermal delivery of active agents is facilitated or rendered possible by formulating them with the compositions according to the present invention.

In a preferred embodiment of the composition according to the first aspect of the invention, component (a) comprises or consists of two mono-alkanoyl glycerol esters, preferably mono-octanoyl glycerol ester and mono-decanoyl glycerol ester. Preferably, position 1 of glycerol is esterified in these compounds.

In a further preferred embodiment of said composition, component (a) further comprises or, in addition to (a)(i), consists of one or more compounds selected from (a) (ii) mono-alkenoyl glycerol esters, alkenoyl being selected from linoleoyl (cis, cis-9,12-octadecadienoyl), oleoyl (9Z-octadec-9-enoyl), elaidinoyl ((E)-octadec-9-enoyl); (iii) an alkanoic acid selected from $C_2$ to $C_{21}$, preferably from $C_6$ to $C_{12}$, most preferred $C_8$ to $C_{10}$ alkanoic acids: and (iv) an alkenoic acid selected from oleic (9Z-octadec-9-enoic), linoleic (cis, cis-9,12-ocfadecadienoic) and elaidic acid ((E)-octadec-9-enoic acid). Particularly preferred alkanoic acids are n-octanoic acid, n-nonanoic acid (in the following briefly referred to as nonanoic acid), and n-decanoic acid.

Further preferred components (a) are the following (1) to (4), wherein in each case component (a) may either consist of or comprise the listed constituents: (1) DecanoylGlycerol (DG), oleic acid, and nonanoic acid; (2) DG, OctanoylGlycerol (OG), oleic acid, and nonanoic acid; (3) OG, oleic acid, nonanoic acid, and monolinolein; (4) DG, OG, and monolinolein; (5) DG, OG and monolein; and (6) DG, OG and ricinoleic acid. Monolinolein is also known as 1-glyceryl linoleate, linoleate being cis, cis-9,12-octadecadienoate. In any of the above defined preferred components (a), n-nonanoic acid may be replaced with n-octanoic acid or n-decanoic acid.

In a further preferred embodiment of the composition according to the first aspect of the invention, component (b) comprises or consists of (ba) cholesterol, and one compound selected from said phosphatidyl cholines and said phosphatidyl glycerols, preferably selected from di-stearoyl phosphatidyl choline and di-stearoyl phosphatidyl glycerol; (bb) cholesterol, a phosphatidyl choline as defined in the first aspect and a phosphatidyl glycerol as defined in the first aspect, the acyl moieties of the phosphatidyl moieties preferably being stearoyl; or (bc) a phosphatidyl choline as defined in the first aspect and a phosphatidyl glycerol as defined in the first aspect.

Accordingly, a preferred component (b) consists of or comprises distearoyl phosphatidyl choline (DSPC), distearoyl phosphatidyl glycerol (DSPG), and cholesterol.

Preferred compositions according to the first aspect of the present invention are those which comprise or consist of any one of the preferred components (a) (1) to (4) as defined above and preferred component (b) consisting of distearoyl phosphatidyl choline (DSPC), and/or distearoyl phosphatidyl glycerol (DSPG), and/or cholesterol. More specifically, preferred compositions according to the first aspect of the present invention are the following: Composition "Lipoleic" (DG, oleic acid, nonanoic acid, DSPC, DSPG, and cholesterol), composition "Lipoleic2" (DG, OG, oleic acid, nonanoic acid, DSPC, DSPG, and cholesterol), composition "Lipoleic3" (DG, OG, oleic acid, nonanoic acid, and DSPC), composition "Lipoleic6" (OG, oleic acid, nonanoic acid, monolinolein, DSPC, DSPG, and cholesterol), composition "Lipolinolein" (DG, OG, monolinolein, DSPC, DSPG, and cholesterol), composition "Liporicino" (DG, OG, ricinoleic acid, nonanoic acid, and DSPC) "Lipolein" (DG, OG, monolein, DSPC, DSPG, and cholesterol), composition "Lipomix" (DSPC, DG, OG, ricinoleic acid, nonanoic acid, monolein), composition "Lipolysoricino" (DG, OG, ricinoleic acid, nonanoic acid and at least one, preferably exactly one of 18:0 lyso phosphatidylcholine, 1-stearoyl-2-hydroxy-glycero-3-phosphocholine and monostearoylphosphatidylcholine (MSPC)), and composition "Liporicino-DLPC" (DLPC, DG, OG, ricinoleic acid, nonanoic acid). In any of the above defined preferred compositions, n-nonanoic acid may be replaced with n-octanoic acid or n-decanoic acid. Preferred amounts of the constituent compounds are provided in the examples enclosed herewith.

According to 3 further preferred embodiment, said composition further comprises or, in addition to (a) and (b), consists of (c) (i) an organic solvent.

Component (c) (i) requires an organic solvent. It is understood that at least one organic solvent is comprised in the composition according to the invention. The term "organic solvent" is known in the art and relates to carbon-based substances commonly used in the chemical industry, capable of dissolving or dispersing one or more substances. Generally speaking, organic solvents are more lipophilic or hydrophobic than water. As a consequence, their log P values are generally greater than zero.

Of particular interest are apolar organic solvents, organic solvents with a smaller dipole moment than water, as well as organic solvents which are hydrophobic, i.e. organic solvents are hardly or not at all miscible with water. Organic solvents according to the invention refer to unsubstituted hydrocarbon solvents like paraffinic, aliphatic and aromatic hydrocarbons and their derivatives containing heteroatoms, like oxygen (e.g., alcohols, ketones, glycol esters), halogens (e.g., carbon tetrachloride), nitrogen (e.g., DMF, dimethyl formamide and acetonitrile) or sulphur (e.g., DMSO: dimethyl sulfoxide).

Preferred organic solvents are methanol, ethanol, alcohols from $C_3$ to $C_{10}$, acetonitrile, butanone, 1,1,1-trifluoroethanol (TFE), hexafluoroisopropanol (HFIP), ethyl acetate, carbon tetrachloride, butanol, dibutyl ether, diethyl ether, cyclohexane, methylene chloride (dichloromethane), hexane, butyl acetate, di-isopropyl ether, benzene, dipentyl ether, chloroform, heptane, tetrachloroethylene, toluene, hexadecane, dimethylformamide (DMF), tetrahydrofurane (THF) and dioxane. Particularly preferred organic solvents are ethanol, alcohols from $C_3$ to $C_{10}$, butanone, 1,1,1-trifluoroethanol (TFE), hexafluoroisopropanol (HFIP), ethyl acetate, butanol, dibutyl ether, cyclohexane, hexane, butyl acetate, di-isopropyl ether, dipentyl ether, heptane, tetrachloroethylene, hexadecane, and dioxane.

In further preferred embodiments, the organic solvent or at least one organic solvent is a water soluble organic solvent. Examples of the water-soluble organic solvent include, but are not limited to, hexaethylene glycol (polyethylene glycol 300), polyethylene glycol 400, ethanol, propylene glycol, glycerin, N-methyl-2-pyrrolidone, dimethylacetamide, and dimethylsulfoxide. Each of these components is commercially available, found in a number of pharmaceutical products, and generally regarded as safe for their intended uses. In further preferred embodiments, the water-soluble organic solvent is a polar aprotic solvent. Of specific interest is a water-soluble organic solvent comprising or consisting of one or a mixture of two or more of a polar aprotic solvents) such as propylene glycol, glycerol, and a polyethylene glycol. Glycerol (or propane-1,2,3-triol) is a colorless, odorless, viscous liquid is widely used in food and pharmaceutical formulations. Also commonly called glycerin or glycerine, it is a sugar alcohol, and is sweet-tasting and of low toxicity. Glycerol has three hydrophilic alcoholic hydroxyl groups that are responsible for its solubility in water and its hygroscopic nature. Propylene glycol (or propane-1,2-diol), a particularly preferred organic solvent, preferably to be used as the only organic solvent, is a diol alcohol, usually a tasteless, odorless, and colorless clear oily liquid that is hygroscopic and miscible with water, acetone, and chloroform. Because of its low chronic oral toxicity, propylene glycol is generally recognized as safe (GRAS) for use as a direct food additive, as well as for cosmetic and pharmaceutical applications. Polyethylene glycols (or PEGs), also known as polyethylene oxides (PEOs) or polyoxyethylenes (POEs), are polyethers. Of particular interest are PEG oligomers and polymers with a molecular mass below 20,000 g/mol, as well as various derivatives, the most common of which is a monofunctional methyl ether PEG (methoxypoly(ethylene glycol)), abbreviated mPEG. Of specific interest are PEG diols having a molecular mass below 8000 g/mol, 4000 g/mol, 1000 g/mol, 800 g/mol, 700 g/mol, or 600 g/mol, and particular PEG diols having a molecular mass of between about 200-500 g/mol, such as hexaethylene glycol, and the better known PEG 300 and PEG 400. As with the other components noted above, the subject PEG compounds are generally recognized as safe for use as a direct food additive, as well as for cosmetic and pharmaceutical applications.

Polar aprotic organic solvents are solvents that share ion dissolving power with protic solvents but lack an acidic hydrogen. These solvents generally have high dielectric constants and high polarity. Examples are N-methyl-pyrrolidone (or N-methyl-2-pyrrolidone), dimethyl sulfoxide, dimethylformamide, dioxane and hexamethylphosphorotriamide. An advantage of polar aprotic solvents is their high solubilizing nature and ability to maintain and/or reduce unwanted ionization of the peptide. Of specific interest is N-methyl-2-pyrrolidone, N-methyl-2-pyrrolidone (NMP, Pharmasolve) is a very strong solubilizing agent and found as a solubilizing agent in certain commercially available pharmaceutical products, it is also found as a volatile component in roasted nuts, and is a versatile solvent miscible with water, ethyl alcohol, ether, chloroform, benzene, ethyl acetate and carbon disulfide.

Particularly preferred organic solvents according to the invention are propylene glycol, dimethylacetamide (DMA), DimethylSulfoxide (DMSO), Ethanol, Glycerol, NMP, Peg 300, Peg 400 and Cremophor, Cremophor preferably being selected from Cremophor EL (polyethoxylated castor oil), Cremophor RH40 (PEG 40 hydrogenated castor oil) and Cremophor RH60). A particularly preferred Cremophor is Cremophor EL. Of a particular interest are mixtures of two or more organic solvents, said two or more organic solvents selected from any of the above disclosed solvents, preferably selected from propylene glycol, dimethylacetamide (DMA), DimethylSulfoxide (DMSO), Ethanol, Glycerol, NMP, Peg 300, Peg 400 and Cremophor, Cremophor preferably being selected from Cremophor EL (polyethoxylated castor oil), Cremophor RH40 (PEG 40 hydrogenated castor oil) and Cremophor RH80). Particularly preferred mixtures are a mixture of propylene glycol with glycerol and a mixture of propylene glycol with NMP, and NMP and Cremophor EL Also preferred is NMP alone. The most preferred solvent is propylene glycol alone.

In a second aspect, the present invention relates to a pharmaceutical or diagnostic composition comprising or consisting of (a) component (a) as defined in the present specification; (b) component (b) as defined in the present specification; (c) (i) an organic solvent; and (d) a pharmaceutically or diagnostically active agent; wherein said pharmaceutically or diagnostically active agent is preferably a peptide, polypeptide, nucleic acid or small organic molecule.

Components (a) and (b) of the pharmaceutical or diagnostic composition according to the invention is as defined herein above.

The pharmaceutical or diagnostic composition furthermore requires components (c) and (d). Component (c), to the extent it requires part (i) thereof, is defined above.

Component (d) of the pharmaceutical or diagnostic composition according to the invention is a pharmaceutically or diagnostically active agent, preferably selected from the group consisting of peptides, polypeptides, nucleic acids and small organic molecules.

Peptides and polypeptides are polycondensates of amino acids, preferably of the 20 naturally occurring proteinogenic amino acids. Generally, peptides have a length from 2 to 30 amino acids and polypeptides a length of more than 30 amino acids. Proteins consist of or comprise one or more peptides and/or polypeptides, it is understood that a pharmaceutical or diagnostic composition according to the invention may also comprise one or more proteins.

The term "peptide" according to the present invention and associated diseases to be treated include: (a) the peptide is Lisinopril also known as Privinil and the disease is hypertension; (b); the peptide is Goserelin, synthetic decapeptide analogue of luteinizing hormone-releasing hormone (LHRH) and the disease is Prostate Cancer; (c) the peptide is Calcitonin and the disease is Osteoporosis; (d) the peptide is Leuprolide and the disease is Prostate Cancer; (e) the peptide is Glucagon the disease is hypoglycemia; (f) the peptide is Integrilin the disease is Anti-coagulation; (g) the peptide is hirudin and is used as anticoagulant and antithrombotic agent, (h) the peptide is desmopressin, which is an analogue of vasopressin and is used therapeutically as an antidiuretic and in the management of bleeding in individuals with some forms of hemophilia and von Willebrand's disease, and wherein the (polypeptide is modified as defined herein above, i.e. by formation of a complex with cyclic compounds of the invention.

Further examples of peptides of interest include, but are not limited to, acetalins (e.g., acetalin 1, 2 and 3 (acetyl plus enkephalin)), adrenocorticotropic hormone (ACTH) and related peptides, adipokinetic hormones (e.g., adrenomedullin), ADP-ribosylation factors (ARF), adrenomedullin peptides, Agouti related peptides, allatostatins, amylin peptides, amyloid peptides, angiotensins and related peptides, annexin, various anti-inflammatory peptides, antimicrobial and related peptides, antioxidant peptides, apelin peptides, apoptosis peptides, Bad and Bag Cell peptides, adrenal medulla peptides, basic fibroblast growth factor (bFGF), bombesins, bradykinins, C-Peptides, C3a peptides, calcitonin and related peptides, CART (cocaine- and amphetamine-regulated transcript) peptides, casomorphins, caspase related peptides, cell adhesion peptides, cholecystokinin-pancreozymin peptides, corticotropin related peptides, cytochromes and related peptides, cytokines (e.g., granulocyte-colony stimulating factor, erythropoietin, etc.), chemokines, defensins, dynorphins, endomorphins, endorphins, endothelins, enkephalins, exendins, fibrinogen and related peptides, fibronectin fragments, galanins, gastric inhibitory peptides (GIPs), gastrins, ghrelins, glucagon, glucagon-like peptides, growth factors, growth hormone related peptides, guanylins, heat shock proteins, hepatitis C virus (HCV) related peptides, high mobility group (HMG) peptide, HIV related peptides, integrins, interleukins, interferons, kinases/phosphatase substrates, luteinizing hormone-releasing hormones and related peptides, matrix metalloproteinases (MMPs), melan-A and mucin related peptides, melanocyte stimulating hormones and analogs, myelin basic proteins (MBPs), myosin, natriuretic peptides, neurokinins, neuromedins, neuropeptide Y and analogs, neuropeptides, neurotensins and related peptides, NF-kB/transcription factors related peptides, orexins, osteocalcin fragments, OVA peptides, oxytocins, vasopressins, desmopressin and related peptides, pancreatic polypeptides, parathyroid hormones and related peptides, peptide YY and analogs, peptidoglycan peptides, phosphopeptides, phytochelatins, pituitary adenylate cyclase activating peptides (PACAPS), prion protein (PrP) fragments, prolactin releasing peptides, proteolipid proteins (PLPs), salusin peptides, saposin related peptides, secretins, selectin related peptides, signal transduction peptides, somatostatins, substance P and analogs, tachykinin related peptide, thrombin related peptides, thrombospondins, thyrotropin releasing hormones and related peptides, TNF peptides, toxins, urotensin related peptides, vasoactive intestinal peptides (VIPs), vasopressin related peptides, viral peptides, and the like.

Of particular interest are peptide hormones, which are a class of peptides that exhibit activity upon entry into the blood stream and have endocrine functions in living animals. Examples of peptide hormones of specific interest include, but are not limited to, glucagon, glucagon-like-peptide, insulin, somatostatin, calcitonin, parathyroid hormone, and the like, and analogues/derivatives thereof. Thus, in certain embodiments, the peptide active agent is a peptide hormone, for example, insulin and the incretin mimetics, such as the exendins and related analogues/derivatives (e.g., chemically synthesized and/or biologically produced exendins such as exendin-3 and exendin-4, liraglutide, glucagon-like peptide-1 (GLP-1), and Taspoglutide, Albiglutide, ZP10 (AVE0010, Lixisenatide), LY 2428757, LY 2189265, GLP-1/GIP Dual Agonist MAR701 and various analogues/derivatives thereof.

The term "(poly)peptide" (i.e., peptide or polypeptide) according to the present invention and associated diseases to be treated include: (a) the (poly)peptide is insulin (Including Insulin Lispro, insulin aspart, and the disease is diabetes; (b) the (poly)peptide is Epoietin alpha and the disease is anemia; (c) the (poly)peptide is Epoietin beta and the disease is anemia; (d) the (poly)peptide is darbepoetin and the disease is anemia; (e) the (poly)peptide is Erythropoietin and the disease is anemia or chronic renal failure; (f) the (poly)peptide is Filgrastim and the indications are Immune disorders, leukemia, diabetic foot ulcers; Leukopenia, and neoplastic diseases; (g) the (poly)peptide is Lenograstim and the indication is Leukopenia; (h) the (poly)peptide is Sargramostin and the indication is Leukopenia; (i) the (poly)peptide is Molgramostin and the indication is Leukopenia; (j) the (poly)peptide is Mirimostim and the indication is Leukopenia; (k) the (poly)peptide is Nartograstim and the Indication is Leukopenia; (l) the (poly)peptide is GCSF and the disease is Chemotherapy induced neutropenia; (m) the (poly)peptide is GMCSF and the indication is Autologous bone marrow transplant; (n) the (poly)peptide is an asparaginase and the disease is cancer; Preferred cancer forms amenable to treatment with asparaginases are lymphoblastic leukemias and large cell lymphoma; (o) the (poly)peptide is Factor VIIa, Factor VIII, Factor IX products (Blood clotting factors) and the disease are Hemophilia A, Hemophilia b; (p) the (poly)peptide is interferon α-alpha-(includes interferon alpha-2a, interferon alpha-2b, interferon alfacon-1, interferon alpha 3n) and the disease is chronic hepatitis B or C and some types of cancer; (q) the (poly)peptide is interferon β (wherein—beta—includes interferon beta-1a, and interferon beta 1b) to treat Multiple Sclerosis and hepatitis; (r) the (poly)peptide is interferon γ (wherein—gamma—includes interferon gamma-1b) and the disease is fibrosis, tuberculosis, meningitis or cancer; (s) the (poly)peptide is human growth hormone (hGH) and the disease is Human growth deficiency in children; (t) the (poly)peptide is somatrem/somatropin and the disease is growth hormone deficiency in children; (u) the (poly)peptide is a superoxide dismutase and the disease is a brain injury; (v) the (poly) peptide is interleukine-2 and the disease is cancer (metastatic renal cancer) or a condition requiring immunostimulation; (w) The human growth hormone (hGH) antagonist B2036 is well known in the art. B2036 is obtained from hGH by the introduction of nine amino acid replacements conferring antagonistic properties and increased receptor affinity (see U.S. Pat. No. 5,849,535). For the purpose of treating acromegaly any other growth hormone (GH)-receptor antagonist (alternatively or in addition to the GH-receptor antagonist B2036) is envisaged; (x) the (poly)peptide is Transtuzumab and the disease is Cancer. It is understood that the term (poly)peptide as used herein includes peptides, polypeptides and proteins.

In a broader sense, "amino acid" refers to any of the naturally occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form, as well as analogues/derivatives thereof. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine). Thus, the amino acids includes protected or modified amino acids, such as acylated amino acids, amidated amino acids and the like.

"Analogue" or "derivative" refers to without limitation any compound which has a structure derived from the structure of the compounds of the present disclosure and whose structure is sufficiently similar to those disclosed herein and based upon that similarity, would be expected, by one skilled in the art, to exhibit the same or similar activities and utilities as the claimed and/or referenced compounds.

Nucleic acids in accordance with the present invention, include DNA, such as cDNA or genomic DNA, and RNA. It is understood that the term "RNA" as used herein comprises all forms of RNA including mRNA, ncRNA (non-coding RNA), tRNA und rRNA. The term "non-coding RNA" includes siRNA (small interfering RNA), miRNA (micro RNA), rasiRNA (repeat associated RNA), snoRNA (small nucleolar RNA), and snRNA (small nuclear RNA).

A preferred nucleic acid is a small interfering RNA. The term "small interfering RNA" (sIRNA), sometimes known as short interfering RNA or silencing RNA, refers to a class of generally short and double-stranded RNA molecules that play a variety of roles in biology and, to an increasing extent, in treatment of a variety of diseases and conditions. Most notably, sIRNA is involved in the RNA interference (RNAi) pathway where the sIRNA interferes with the expression of a specific gene (see, e.g. Zamore Nat Struct Biol 2001, 8(9):746-50; Tuschl T. Chembiochem. 2001, 2:239-245; Scherr and Eder, Cell Cycle. 2007 February; 6(4):444-9; Leung and Whittaker, Pharmacol Ther. 2005 August; 107 (2):222-39; de Fougerolles et al., Nat. Rev. Drug Discov. 2007, 6: 443-453).

The term "small organic molecule" is established in the art. It refers to molecules with a carbon skeleton, having a molecular weight which is preferably below 2000, 1500, 1000, 900, 800, 700, 600, 500, 400 or 300 Daltons.

The term "small organic molecule" as used herein includes the agents listed in the following, wherein the corresponding medical indication is also provided: (a) Synthetic and natural Antibiotics: derivatives of Pyridonic ring (Nalidixix acid, Oxolinic acid), Penicillin derivatives (Benzyl-Penicillin, Phenoxymethyl-penicillin, Meticillin, Oxacillin, Ampicillin, Amoxycillin, Pivampicillin, Talampicillin, Carbenicillin, Ticarcillin) Cefalosporin derivatives (Cefalosporin C, Cefaloglycine, Cefotaxime, Cefinetazole, Cefradin, Cefalexin, Cefalotin, Cefaloridin, Cefazolin, Cefsulodin, Cefacetril, Cefapyrin, Cefuroxime, Cefamandol, Cefoxitin, Cefazol Cefoperazone, Cefiriaxone) Antibiotics aminoglycosides (Streptomycin, Neomycin, Gentamicin, Tobramycin, Amikacin), Polyenes (Nistatin, Amphotericin B), Anti-Tubercolosis (Para-amino salicylic acid) (b) Neurotransmitters: Catecholamines (Adrenaline, Noradrenaline, L-Dopamine, Dopamine, Carbidopa), L-Dopa, Melevodopa (Levodopa methyl ester and other esters with alcohols from $C_2$ to $C_{18}$ including ester with glycerol and propylene glycol) Serotonin, γ-amino-butyric acid (GABA); (c) Anti-inflammatory and Analgesic non steroids: Salicylic Acid, Acethylsalicylic acid; Phenylacetic acids: Ibuprofen, Phenoxyprofen, Ketoprofen, Naproxen, Diclofenac; Etherocyclic acetic acids: Indomethacine, Clometacine, Sulindac, Zomepirac, Thiapropheic acid; Antranilic acids: Mephenamic acid, Fluphenamic acid, Meclophenamic acid, Tolphenamic acid, Niflumic acid. (d) Anti-coagulants: Heparin (either sodium or calcium derivatives), Dermatan Sulfate, Enoxaparin Sodium, Dalteparin Sodium.; (e) Diuretics: Furosemide, Bumetanide, Etacrinic acid, Tienilic acid, Triamterene, Amiloride; (e) VariuosVarious: Valproic acid (anti-epilectic), Clavulanic acid (inhibitor of J-Lactamases), Lithium salts (anti-Psychotic).

In a preferred embodiment of the pharmaceutical or diagnostic composition according to the invention, component (a) accounts for about 20% to about 80% w/w of said pharmaceutical or diagnostic composition. In a more preferred embodiment of the pharmaceutical or diagnostic composition according to the invention, component (a) accounts for about 30% to about 60% w/w of said pharmaceutical or diagnostic composition.

In a further preferred embodiment of the pharmaceutical or diagnostic composition, component (b) accounts for about 60% to about 1% w/w of said pharmaceutical or diagnostic composition. In a more preferred embodiment of the pharmaceutical or diagnostic composition, component (b) accounts for about 40% to about 5% w/w of said pharmaceutical or diagnostic composition.

In a further preferred embodiment of the pharmaceutical or diagnostic composition, component (c) accounts for 1 to 60%, preferably 1 to 35% or 10 to 25% w/w of said pharmaceutical or diagnostic composition.

In a preferred embodiment of the pharmaceutical or diagnostic composition according to the invention, component (c) of said pharmaceutical or diagnostic composition further comprises (c)(ii) a cyclic compound of formula (I), or said component (c), in addition to (c)(i) or instead of (c)(i) consists of (c)(ii) a cyclic compound of formula (I), or the composition of the first aspect of the invention, said composition further comprising or, in addition to (a) and (b), consisting of (cXii) a cyclic compound of formula (I), formula (I) being defined as follows

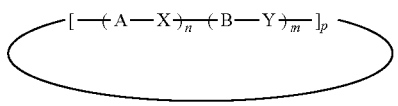

wherein A, B independently in each occurrence is alkane-i,j-diyl having k carbon atoms, i and independently j being less than or equal k and k being selected from 1 to 10, wherein said alkane-i,j-diyl (1) may comprise one or more double bonds; (2) is optionally substituted; and/or (3) comprises a cycle, wherein the total number of cycles being cyclic sugars in said compound is selected from 0 to 4 and is less than p·(n+m); X, Y independently in each occurrence is a biocompatible functional group comprising at least one oxygen atom or two sulphur atoms; n, m independently of each other are selected from 0 to 20; p is selected from 1 to 10; n+m is equal or greater than 1; and p·(n+m) is selected from 3 to 30; wherein said cyclic compound is capable of forming a complex with a protonated primary amino group, a protonated secondary amino group, a protonated guanidinium group, and/or a metal ion.

Accordingly, envisaged are compositions according to the first aspect of the present invention which consist of components (a) and (b), and in addition a cyclic compound of Formula (I) as defined above. Alternatively, said composition according to the first aspect may comprise further constituents, preferred further constituents being specified herein above. As regards the pharmaceutical or diagnostic composition according to the invention, said pharmaceutical or diagnostic composition may consist of components (a), (b) and (d), and furthermore component (c). Component (c) in turn may consist of (c)(i), i.e., an organic solvent, only, or may consist of (c)(ii), i.e., an above defined cyclic compound only, or component (c) may consist of both a organic solvent and an above defined cyclic compound. Alternatively, further constituents may be comprised in the pharmaceutical or diagnostic composition according to the invention, preferred further constituents being disclosed herein such as the preferred further constituents of components (a) and (b).

In case both a cyclic compound and an organic solvent are present, preferred amounts are as follows. 10 to 20% w/w of a composition according to the invention consisting of components (a), (b) and (c)(i) plus 80 to 90% w/w of said cyclic compound. Also about 40% w/w of said composition consisting of components (a), (b) and (c)(i) plus 60% w/w of said cyclic compound may be used. Particularly preferred is about 90% w/w of said composition consisting of components (a), (b) and (c)(i) plus 10% w/w of said cyclic compound.

The use of such cyclic compound is preferred in those cases, wherein said active agent comprises one or more protonated primary amino groups, protonated secondary amino groups and/or protonated guanidinium groups and/or said active agent forms a salt with a metal ion, preferred metal ions being selected from $Na^+$, $K^+$, $Ca^{2+}$ and $Mg^{2+}$.

The curved line in formula (I) stands for one single bond connecting covalently the first occurrence of A with the last occurrence of Y. The terms "first occurrence" and "last occurrence", respectively, relate to the non-cyclic counterpart of a compound of formula (I), said non-cyclic counterpart having the formula $[-(-A-X-)_n-(-B-Y-)_m-]_p$.

The term "alkane-i,j-diyl" relates to an alkane with two free valences at carbon atoms i and j. Preferred alkane-i,j-diyls are disclosed below in terms of the corresponding monomers.

It is understood that the cyclic compounds according to the invention may be characterized in either one of the following ways. First, they may be characterized in terms of building blocks A and B, wherein said building blocks are linked by functional groups X and Y. Secondly, and to the extent said functional group X, Y is further defined as being, for example, an ester group (—C(=O)—O—) or amide group (—C(=O)—NH—), cyclic compounds according to the invention may be characterized in term of the monomers giving rise to said compounds. To explain further, monomers include—in case of polyesters—hydroxy acids and—in case of polyamides—amino acids. The difference between a characterization in terms of building blocks A, B and monomers such as hydroxy acids and amino acids is as follows. The monomers include those functional groups, such as —COOH, —OH in case of an amino acid monomer and —COOH, —NH2 in case of an amino acid monomer, which, upon formation of a cyclic compound of the invention from said monomers, give rise to functional groups X, Y such as ester or amide. The building blocks A and B on the other side do not include the functional groups X, Y. As a consequence, a cyclic polyester comprising monomers of lactic acid may either be characterized in terms of the monomer lactic acid or in terms of the building block A and/or B which is ethane-1,1-diyl. Similarly, the monomer glycolic acid has its counterpart in a building block A and/or which is methylene (—$CH_2$—). Accordingly exemplary/preferred values of k are 2 and 1.

Preferred alkane-i,j,-diyls include 1,k-diyls as well as alkane-i,j-dlyls wherein i equals j. An example of an alkane-i,i-diyl is ethane-1,1-diyl is described above.

The term "substituted" is understood to include any substituents. Preferably, "substituted" refers to a monosubstitution. Preferred carbon atoms to be substituted in the alkane-i,j-diyl are carbon atoms i and/or j. It is understood that substituents, if present, introduce further carbon atoms in addition to the k carbon atoms of the alkane-i,j,-diyl into the building block A or B. In FIG. 2 enclosed herewith, substituents are designated "R".

Preferred substituents include linear or branched alkyl, preferably with between 1 and 10 carbon atoms, the linear or branched alkyl substituents optionally being substituted with one or more of —OH, —COOH and halogen. Further preferred substituents include substituted or unsubstituted aryl or heteroaryl. Preferred aryl substituents are phenyl, methyl-phenyl such as 4-methyl-phenyl and hydroxy-phenyl such as 4-hydroxy-phenyl. Further preferred substituents of the alkane-i,j-dlyl are one or more of —OH, —COOH and halogen.

The term "cycle" refers to building blocks comprising a cyclic structure such as the building blocks of nonactin (see below). Other examples of a cycle within a monomer is the cyclic form of a sugar or of a sugar derivative. Cyclic sugars of the invention include pyranoses and furanoses such as glucopyranose. If present, the number of monomers being or comprising cyclic sugars is less than the total number of monomers of the compound of the Invention. More preferred, the number of monomers consisting of or comprising cyclic sugars, if present, is 1, 2 or 3. Also, it is preferred that not more than two monomers consisting of or comprising cyclic sugars are directly linked to each other, wherein the link, i.e., the functional group X or Y, respectively, is —O—, said —O— being a glycosidic bond. The term "sugar derivative" includes sugars wherein one, more or all hydroxy groups are acetylated and/or alkylated.

It is understood that the alkane-i,j-dyl may be cyclic. Alternatively or in addition, a substituent of the alkane-i,j- dyl may be cyclic. Also envisaged are cycles comprising atoms of both the alkane-i,j-diyl and the substituent.

The term "biocompatible functional group comprising at least one oxygen atom or two sulphur atoms" refers to two classes of functional groups, wherein one class is a class of oxygen-comprising functional groups and the other class is a class of functional groups comprising or consisting of two sulphur atoms, wherein the functional groups of both classes do not give rise to adverse reactions or side effects if administered to a living organism to be treated with the pharmaceutical composition of the invention or to be diagnosed using the diagnostic composition of the invention. The term "biocompatible" is equivalent to "generally recognized as safe (GRAS)". Means for assessing biocompatibility are well known in the art, include in vitro tests performed on cell lines, in vivo tests on animals as well as clinical tests on human being and do not have to be further detailed here. Any test required or recommended by regulatory authorities for the assessment of whether a compound is generally recognized as safe (GRAS), is preferably employed for identifying those cyclic compounds whose oxygen-containing functional group(s) is/are biocompatible. Preferably the oxygen atom of said biocompatible functional group comprising at least one oxygen atom is available for forming a complex with said protonated primary amino group, said protonated secondary amino group or said protonated guanidinium group. Analogously, preferably one or both of the sulphur atoms of the biocompatible functional group comprising two sulphur atoms is available for complex formation. Preferred biocompatible functional groups comprising at least one oxygen atom include ester (—C(=O)—O—), amide (—C(=O)—NH—), ether (—O—), oxime (—C=N—O—), thioester (—C(=O)—S— as well as —C(=S)—O—), hemiacetal, acetal and sulfoxide (—S(=O)—). More preferred are ester (—C(=O)—O—), amide (—C(=O)—NH—) and ether (—O—). Preferred biocompatible functional groups comprising two sulphur atoms are disulfide (—S—S—) and dithioester (—C(=S)—S—). More preferred is disulfide (—S—S—). Functional groups comprising at least one oxygen atom which are not biocompatible include peroxide.

In a preferred embodiment, all occurrences of A are the same. Alternatively or in addition, all occurrences of B may be the same. If both all occurrences of A are the same, for example a group A, such as ethane-1,1-diyl and all occurrences of B are the same, for example a group $B_1$ such as methylene, an alternating pattern of building blocks is obtained. The variable p defines the number of repetitions of said pattern within the compound of the invention. Furthermore, A=B may be valid for all occurrences of A and B.

Similarly, all occurrences of X may be the same. Alternatively or in addition, all occurrences of Y may be the same. Furthermore, X=Y may be valid for all occurrences of X and Y.

The lower limit of 3 on the values of p·(n+m) ensures that at least three oxygen atoms are comprised in the compound of the invention. Preferably, at least four oxygen atoms are comprised in the compound of the invention. This may be achieved by a minimal value of p·(n+m) of 4. Preferred ranges of p·(n+m) include 3 to 20, 3 to 10, 4 to 10 and 4 to 8.

In a preferred embodiment, said compound is selected from a (i) cyclic polyester; (ii) cyclic polyamide; (iii) cyclic polyether; (iv) cyclic polyoxime; (v) polythioester; (vi) polymer of aminoxy acids; (vii) poly-disulfide; and (viii) a cyclic compound belonging to more than one of (i) to (vii). More preferred are cyclic polyesters, cyclic depsipeptides and cyclic polyethers. Yet more preferred are cyclic polyesters.

The term "cyclic" refers to compounds of the invention such as polyesters, polyorthoesters, polyamides, depsipeptides, polyethers and polyoximes of the invention which contain a ring. When used to designate a feature of the compound of the invention as a whole, which is the case here, the term "ring" refers to a ring which includes all functional groups X and Y. The functional group providing closure of said ring may be the same or different from the functional group giving rise to the classification as polyester, polyorthoester, polyamide, depsipeptide, polyoxime or polyether. Preferably, the functional group providing closure is the same as the functional group giving rise to said classification, i.e., in case of a cyclic polyester one further ester linkage is formed when the corresponding linear form is converted into the cyclic form. The term "corresponding linear form" designates a polymer or oligomer (the term "polymer" as used herein includes oligomers) which has a given number of monomers linked together to form a linear polymer, wherein said given number is the same as the number of monomers in the cyclic compound of the Invention. In other words, the number of monomers one the one side and on the other side the number of ester functionalities (in case of cyclic polyesters), orthoester functionalities (in case of cyclic polyorthoesters), amide functionalities (in case of cyclic polyamides) or the combined number of ester and amide functionalities (in case of cyclic depsipeptides) are the same.

The term "polymer" is understood to comprise both polymers in the narrow sense, i.e. molecules formed from a plurality of building blocks or one or more than one type (in the latter case said polymers are also referred to as co-polymers), wherein upon formation of the polymer from the building blocks no further molecule(s) such as water is formed, as well as polycondensates, i.e. polymers according to the present invention, wherein upon formation of the polymer from its building blocks (a) further molecule(s) such as water is/are formed in addition to the polymer.

The term "polyester" as used herein relates to compounds which comprise at least two ester functionalities, i.e. two —C(=O)—O— groups. Cyclic esters are also referred to as lactones. The building blocks of polyesters and depsipeptides (see below) are or include, respectively, hydroxy acids. Preferred building blocks or monomers according to the invention are alpha-hydroxy acids and beta-hydroxy acids. Also preferred are hydroxy acids with up to ten carbon atoms, wherein any number below ten is explicitly included in the scope of the invention. As such, preferred alpha-hydroxy acids include alpha-hydroxy acids with two, three, four, five, six, seven, eight, nine or ten carbon atoms or up to 20 carbon atoms. Preferred beta-hydroxy acids include beta-hydroxy acids with three, four, five, six, seven, eight and nine carbon atoms. Specific preferred alpha-hydroxy acids are glycolic acid, lactic acid, alpha-hydroxy n-butyric acid, alpha-hydroxy n-pentanoic acid and alpha-hydroxy n-hexanoic acid. Preferred beta-hydroxy acids include beta-hydroxy propionic acid, beta-hydroxy n-butyric acid, beta-hydroxy n-pentanoic acid and beta-hydroxy n-hexanoic acid. Also envisaged are hydroxy acids with branched alkyl side chains such as beta-hydroxy i-butyric acid and alpha-hydroxy i-pentanoic acid, as well as hydroxy acids with hydroxyalkyl side chain. Preferably, said hydroxyalkyl side chain carries a terminal hydroxy group. Such cyclic polyesters, polyorthoesters, polyamides, depsipeptides, polyethers and polyoximes of the invention may carry one or more free hydroxyl moieties on the side chain for further exploitation such as derivatization by esterification. Furthermore envisaged are hydroxy acids with aromatic side chains. Hydroxy acids with aromatic side chains include any of the above mentioned aliphatic acids, wherein said acids are substituted with a phenyl group. The phenyl group in turn may be substituted. An example is 2-Phenyl-2-hydroxyacetic acid (mandelic acid). Cyclic polyesters according to the invention may consist of one type of monomer or a plurality of types of monomers. Said plurality may, for example, be a plurality of alpha-hydroxy acids or a mixture of alpha-hydroxy acids and beta-hydroxy acids. In a preferred embodiment, alpha-hydroxy acids and beta-hydroxy acids alternate.

It is understood that polyesters may arise from polymerization of hydroxy acids. Alternatively, polyesters may arise from polymerization of a di-alcohol with a di-acid. The same applies mutatis mutandis to polyamides and depsipeptides of the invention.

The term "orthoester" as used herein relates to compounds comprising a carbon atom linked to three alkoxy groups. Accordingly, polyorthoesters are compounds comprising at least two such functionalities. Cyclic polyorthoesters are valence tautomers of cyclic polyesters (see McGeary and Bruget (2000)). Both tautomeric forms are suitable to practice the present invention. It is furthermore understood that the term "polyorthoester" is to be subsumed under the term "polyester" of the invention.

The term "polythioester" according to the Invention refers to compounds comprising at least two thioester functionalities, i.e., (i) at least two —C(=O)—S— groups, (ii) at least two —C(=S)—O— groups, or (iii) at least one —C(=O)—S— group and at least one —C(=S)—O— group.

Also envisaged are cyclic compounds of the invention which are cyclic poly-dithio-esters. The term "poly-dithioester" as used herein refers to compounds comprising at least two dithioester functional groups (—C(=S)—S—).

The term "polyamide" according to the invention refers to compounds comprising at least two amide functionalities, i.e. two —C(=O)—NH— groups. Cyclic amides are also designated lactames. The amide bond is also referred to as peptide bond, in particular in the context of peptides. Preferred building blocks or monomers of cyclic polyamides according to the invention are alpha-amino acids and beta-amino acids. Also depsipeptides (see below) comprise alpha-amino acids. Further preferred are amino acids with up to ten carbon atoms, wherein any number below ten is explicitly included in the scope of the invention. As such, preferred alpha-amino acids include alpha-amino acids with two, three, four, five, six, seven, eight, nine or ten carbon atoms. Preferred beta-amino acids include beta-amino acids with three, four, five, six, seven, eight and nine carbon atoms. Specific preferred alpha-amino acids are the naturally occurring amino acids. Particularly preferred alpha-amino acids are Gly, Ala, Val, Leu, Ile, Met and Phe. The occurrence of one or more of the remainder of the naturally occurring amino acids (such as Cys, Asn, Gln, Pro Ser, Thr, Trp, Tyr), where appropriate, is also deliberately envisaged. Further alpha-amino acids are alpha-amino butyric acid and alpha-amino i-butyric acid. Preferred beta-amino acids include beta-alanine. Furthermore, gamma-amino butyric acid may be used as the only or one of the monomers in the cyclic polyamides or depsipeptides of the invention. Cyclic polyamides according to the invention may consist of one type of monomer or a plurality of types of monomers. Said plurality may, for example, be a plurality of alpha-amino acids or a mixture of alpha-amino acids and beta-amino acids. In a preferred embodiment, alpha-amino acids and beta-amino acids alternate.

The term "polyamide" includes also compounds of the invention the monomers of which are alpha and beta aminooxy acids (see, for example, Yang et. al. *J. Am. Chem. Soc.*, 2002, 124, 12410-12411) and related compounds.

The term "depsipeptide" is known in the art and designates herein compounds which comprise or consist of alpha-hydroxy acids and alpha-amino acids, which are linked to each other by ester linkages between the hydroxy group of an alpha-hydroxy acid and the carboxyl group of either a hydroxy acid or an amino acid as well as by amid linkages between the amino group of an alpha-amino acid and the carboxyl group of either a hydroxy acid or an amino acid. More than one type of alpha-hydroxy acid and/or alpha-amino acid may be present in a depsipeptide. On the other hand, also depsipeptides, wherein only one type of alpha-hydroxy acid and/or only one type of alpha-amino acid occurs, are include in the scope of the invention. Alpha-hydroxy acid monomers and alpha-amino acid monomers may alternate. A strictly alternating sequence would imply an even number of monomers in the cyclic depsipeptide of the invention. Alternatively, one or more ester-linked stretches consisting of a plurality (such as two, three, four, five, six, seven, eight, nine or more) of alpha-hydroxy acid monomers may be followed by one or more amid-linked stretches consisting of a plurality (such as two, three, four, five, six, seven, eight, nine or more) of alpha-amino acids. Preferred alpha-amino acids and alpha-hydroxy acids are described herein above.

The term "polyether" refers to compounds comprising at least two ether functional groups. An ether functional groups is represented by —O—, wherein the carbons directly adjacent to the oxygen atom are not substituted by heteroatoms. For example, biocompatible polymers like PEGs are to be subsumed under the term "polyether".

The term "polyoxime" refers to compounds comprising at least two oxime functional groups (—C=N—O—). An exemplary cyclic polyoxime is shown in FIG. 2.

A further preferred class of cyclic compounds of the invention are cyclic polymers of aminoxy acids, preferably of alpha-aminoxy acids. The oxygen-containing functional group in cyclic polymers of aminoxy acids is —C(=O)—NH—O— or —C(=O)—N(OH)—. Polymers of aminoxy acids wherein the functional group is —C(=O)—N(OH)— are also referred to as polyhydroxamic acids.

Another preferred class of cyclic compounds of the invention are cyclic poly-disulfides. The term "poly-disulfide" as used herein refers to compounds comprising at least two disulfide functional groups (—S—S—). An Example is shown in FIG. 2. Disulfides are known to be reversible/breakable under physiological conditions in vivo by reducing agents naturally occurring in the human or animal body such as glutathione and other endogenous mercaptans.

The terms "polyester", "polyamide", "polyether", "polyoxime" and "cyclic polymer of aminoxy acids" include compounds of the invention wherein for all occurrences X=Y=ester (in case of polyester), for all occurrences X=Y=amide (in case of polyamide) etc. Also included are compounds wherein a majority, i.e. more than 50% of all occurrences of X and Y together, are ester (in case of polyester), amide (in case of polyamide), ether (in case of polyether) or oxime (in case of polyoxime), respectively. Accordingly, also included are compounds wherein out of a total of k functional groups (X, Y), k−1 functional groups are of one particular type such as ester, and one functional group is of a different type such as amide. In other words, a preferred class of cyclic compounds of the invention are cyclic polyesters where a single amide bond replaces a single ester bond generating a mono-amide cyclic polyester; In a further preferred embodiment, the cyclic polyester is composed by alpha-hydroxy acids and a single amide bond (CO—NH—) replaces only one ester bond (CO—O—). In a further preferred embodiment, the cyclic polyester is composed of alpha-hydroxy acids and a single amino acid is used to replace a single alpha-hydroxy acid. Such class of cyclic compounds, maintaining the main features of the all polyester bonds cyclic structure, can be synthesized and produced more easily with superior yields. Another example of this type of cyclic compound are mono-oxo crown ethers such as the compound shown in FIG. 2, bottom, right. Such compounds have k−1 ether groups and one ester group.

The term "cyclic compound belonging to more than one of (i) to (vii)" includes poly-ester-co-ethers, depsipeptides, poly-ester-co-oximes, poly-amide-co-esters and the like. A preferred embodiment of said cyclic compound belonging to more than one of (i) to (iv)" are Peg-polyesters (also referred to as oxo-PEGs including mono-oxo PEG and di-oxo PEG, see also FIG. 2): In such embodiment at least two oligomers comprising or consisting of a Peg or a polyether, said Peg or polyether, respectively, having at the two ends a hydroxyl group and a carboxylic acid, are fused together in a single cyclic structure by forming at least two esters bonds (cyclic poly-ether-co-ester). An example of such a cyclic compound can be found in patent application JP55143981 (Okahara Mitsuo; Matsushima Kenji) (see also K. Matsushima, N. Kawamura, Y. Nakatsuji and M. Okahara, (1982), Bull. Chem. Soc. Jpn, 55, 2181-2185).

Further preferred poly-ester-co-ethers are oxo-crown ethers, i.e., crown ethers with one or more oxo groups. A particularly preferred representative of this class of compounds is mono-oxo 18-crown-6 as shown below.

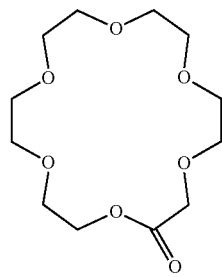 [SMILES: O=C1COCCOCCOCCOCCOCCO1]

In a further preferred embodiment, the cyclic compound of the invention is a cyclic compound belonging to more than one of polyester, polyamide, polyether, polyoxime and cyclic polymer of aminoxy acids. In this embodiment, one or more occurrences of X or Y is —C(=O)—NH—O—.

It is understood that preferred monomers of the polyesters, polyamides, polyethers, polyoximes and cyclic compound belonging to more than one of (i) to (vii) as defined herein above, i.e., preferred hydroxy acids, preferred amino acids and the like, at the same time provide a definition of preferred building blocks A, B of the main embodiment. By removing the hydroxy and the carboxylic acid group from a hydroxy acid disclosed above, an alkane-i,j-diyl is obtained, wherein positions i and j are the positions of the hydroxy and the carboxylic acid group. Similarly, by removing the amino and the carboxylic acid group from a amino acid disclosed above, an alkane-i,j-diyl is obtained, wherein positions i and j are the positions of the amino and the carboxylic acid group. In general, by removing those functional groups present on said monomers which give rise to the functional groups designated X, Y in the main embodiment (for example, —OH and —COOH give rise to —C(=O)—O—; —NH2 and —COOH give rise to —C(=O)—NH—), said alkane-i,j-diyl is obtained. The obtained alkane-i,j-diyl provides a building block A or B which may be bound to any biocompatible oxygen-containing functional group X or Y within the cyclic compound of the invention. It is furthermore understood, that, in line with the main embodiment, said alkane-i,j-diyl may comprise one or more double bonds, may be substituted as defined above, and/or may comprise a cycle as defined above.

The terms "complex" and "complexation" are well known in the art and refer to a reversible association of molecules, atoms, or ions through non-covalent chemical bonds. Usually two interaction partners, a complexing agent having a plurality of functional groups and a small molecule, atom or ion bound by said plurality of functional groups are implied. As used herein, the term complex is not confined to metal ions bound to a complexing agent. It relates in general to complexes between a compound of the invention and a cation or cationic group.

The cyclic compounds of the invention provide oxygen-containing functional groups, the oxygen being available for complex formation. An example of an oxygen atom is the ether oxygen in the cyclic polyethers of the invention. The cyclic polyesters, polyamides and, depsipeptides of the invention provide carbonyl groups (which are part of the amide and ester functionalities) as functional groups involved in complex formation. The cyclic polyorthoesters of the invention provide oxygen atoms (which are part of the alkoxy groups in said polyorthoesters) as functional groups involved in complex formation.

Further preferred embodiments of the recited cyclic compounds are disclosed in EP 2068934, the content of which is herewith incorporated by reference in its entirety.

In particular, a preferred cyclic compound is a crown ether. In a preferred embodiment, said crown ether is selected from the group consisting of 18-crown-6,12-crown-4,15-crown-5, benzo-18-crown-6, dibenzo-18-crown-6,12-crown-4,15-crown-5, (12-crown-4)-2-methanol, 18-crown-6 tetracarboxylic acids, (18-crown-6)-2-methanol, benzo-15-crown-5, dibenzo-15-crown-5,4'-aminobenzo-15-crown-5,4'-amino-benzo-18-crown-6 and calixarenes such as calix[4]arene, calix[6]arene, calix[8]arene, and calix[6]arene-hexaacetic acid hexaethylester.

A further preferred cyclic crown compound is A crown ether of formula (II)

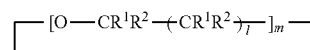

wherein
m is 4, 5, 6, 7, or 8 and i is, independently for each occurrence, 1 or 2;
each occurrence of $R^1$ and $R^2$ is independently selected from hydrogen; linear or branched and substituted or unsubstituted $C_1$ to $C_{10}$ alkyl, alkenyl and alkinyl; and substituted or unsubstituted aryl with up to 10 ring atoms; or $R^1$ and $R^2$ together form an oxo group; at least one occurrence in the crown ether of $R^1$, $R^2$ and the carbon to which $R^1$ and $R^2$ are attached, said carbon being bound directly to an ether oxygen of formula (II), form together a group of formula (III)

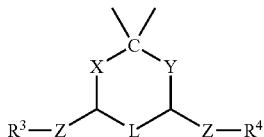

wherein

L is a linker which is absent or selected from a covalent bond and $(CR^5R^6)_n$, each occurrence of $R^5$ and $R^6$ being independently selected from hydrogen; linear or branched and substituted or unsubstituted $C_1$ to $C_{10}$ alkyl, alkenyl and alkinyl; and substituted or unsubstituted aryl with up to 10 ring atoms, n being 1, 2 or 3;

X and Y, independently from each other, are selected from O and S;

Z, independently for each occurrence, is absent or an electron-withdrawing group;

$R^3$ and $R^4$, independently for each occurrence, are selected from hydrogen; linear or branched and substituted or unsubstituted $C_1$ to $C_{10}$ alkyl, alkenyl and alkinyl; substituted or unsubstituted aryl with up to 10 ring atoms; $H(OCH_2CH_2)$— and $H(OCH_2CH_2)_kO$—, wherein k is an integer number from 1 to 10;

wherein substituents, if present, are selected from OH, O—$CH_3$ and halogens. Preferred halogens are F, Cl and Br.

The rectangular line in formula (II) stands for one covalent single bond connecting the oxygen atom of the first occurrence of the moiety in square brackets with the last carbon atom of the last occurrence of the moiety in square brackets.

The building block in square brackets is repeated m times. A preferred value of m is 6. Further preferred values are 5 and 7. Each building block, depending on the value of i, comprises two or three carbon atoms forming the crown ether ring, wherein preference is given to i=1, i.e., two carbon atoms of each building block contributing to the crown ether ring. The terms "crown ether ring", "crown ether macrocycle" and "ring structure of said crown ether" refer to the ring or macrocycle formed by all oxygens and carbons shown in formula (II). In case of the preferred embodiment of m being 6 and i being 1, this ring or macrocycle is the ring or macrocycle of 18-crown-6, i.e., it comprises 6 oxygens and 12 carbons, giving rise to an 18-membered macrocycle.

In addition to the orthoester functionality, the crown ether may be further modified by $R^1$ and $R^2$ as defined above. Within the definition of $R^1$ and $R^2$, linear alkyl, alkenyl and alkinyl groups are preferred over branched alkyl, alkenyl and alkinyl groups. Furthermore, unsubstituted groups $R^1$ and $R^2$ are preferred. The term "substituted" refers to the presence of substituents, said substituents being selected from OH and halogen. Within alkyl, alkenyl and alkinyl, preference is given to alkyl. Preferred chain length of alkyl, alkenyl and alkinyl are $C_1$ to $C_6$, more preferred $C_1$ to $C_4$. Aryl preferably is a five- or six-membered ring. Preferred aryl groups include phenyl.

Preference is given to embodiments wherein each occurrence of $R^1$ and $R^2$, to the extent they do not form a group of formula (III), is hydrogen. In further preferred embodiment, each of $R^1$ and $R^2$, to the extent they do not form a group of formula (III) and not an oxo group, is hydrogen.

In the crown ethers of formula (II), at least one carbon atom which is bound directly to an ether oxygen of formula (II) is modified as required by formula (III). As a consequence, the crown ether comprises at least one orthoester or a thio-analogue thereof. In thio-analogues, one or both of X and Y are S. As used in the following, the term "orthoester" embraces said thio-analogues. The orthoester can be seen as a derivative of one equivalent of a crown ether having a carbonyl group adjacent to an ether oxygen—such crown ether comprising an ester group—and two equivalents of an alcohol or thiol. It is understood that the carbon atom with two free valences as shown in formula (III) is part of the crown ether ring.

If the linker L is present, the orthoester is cyclic. The cycle comprises X and Y. Cyclic orthoesters can be considered as derivatives of a crown ether comprising an ester group, said derivative being obtainable by treating said crown ether comprising an ester group with a diol (or glycol) or a thio-analogue thereof such as a dithiol. Also alcohols with one hydroxy and one thiol group are envisaged and subsumed under the term "thioanalogue of a diol". In case of a vicinal diol or thio-analogue thereof such as ethylene glycol or propylene glycol, L in the resulting cyclic orthoester is a covalent bond. In case of an N,N+2 diol (N and N+2 being the numbers of the carbon atoms carrying the hydroxy groups) or thio-analogue thereof, N+2 not exceeding the number of carbon atoms in said diol or thio-analogue thereof, L in the resulting cyclic orthoester is a methylene group or $CR^5R^6$, $R^5$ and $R^6$ being defined above and further specified below. Similarly, in case of an N,N+3 diol or thio-analogue thereof, N+3 not exceeding the number of carbon atoms in said diol or thio-analogue thereof, L in the resulting cyclic orthoester is $CH_2CH_2$ or $CR^5R^6CR^5R^6$, $R^5$ and $R^6$ being defined above. Said thiol or thio-analogue thereof may comprise further functional groups. Within the definition of $R^5$ and $R^6$, linear alkyl, alkenyl and alkinyl groups are preferred over branched alkyl, alkenyl and alkinyl groups. Furthermore, unsubstituted groups $R^5$ and $R^6$ are preferred. The term "substituted" refers to the presence of substituents, said substituents being selected from OH and halogen. Within alkyl, alkenyl and alkinyl, preference is given to alkyl. Preferred chain length of alkyl, alkenyl and alkinyl are $C_1$ to $C_6$, more preferred $C_1$ to $C_4$. Aryl preferably is a five- or six-membered ring. Preferred aryl groups include phenyl. As indicated above, preference is furthermore given to embodiments wherein each occurrence of $R^5$ and $R^6$ is hydrogen.

A preferred vicinal diol comprising further functional groups is tartaric acid; see, for example, formulae (IV) to (VII), (IX) and (X). As shown in particularly preferred structures below, the carboxylic groups of the tartaric acid moiety of an orthoester may be esterified with an alcohol, e.g. glycerol or ethanol; see, for example formulae (IX) and (X). Particularly preferred are diethyl tartrate orthoesters of oxo-crown ethers. In that case the electron-withdrawing groups Z are ester groups. The free hydroxyl groups of glycerol are available for further derivatization, if desired. Such further derivatization may include the attachment of polymers or oligomers such as polyethylene glycol (PEG) or esterification with fatty acids, said fatty acids preferably being saturated or unsaturated $C_4$ to $C_{20}$ alkanoic acids. Such further derivatisation may be useful in enhancing or modifying biocompatibility and/or delivery across membranes, mucosae, or to target sites within a cell or an organism.

A further preferred vicinal diol comprising further functional groups is 2,3-dihydroxy-propanoic acid; see, for example, formula (XII). The carboxylic group of 2,3-dihydroxy-propanoic acid may be further derivatized, for example esterified; see, for example, the option for R in formula (XII).

If L is absent, X and Y do not form part of a cycle. In that case, the free valences of the carbon atoms bound to X or Y, respectively and bearing Z (or $R^3$ and/or $R^4$ in case of absence of Z) are saturated with hydrogens. If L is absent, the orthoesters can be considered as derivatives of a crown ether comprising an ester group and an alcohol or thiol or mixtures thereof. Preferred crown ethers of the invention comprising acyclic orthoesters are the crown ethers of formulae (VIII) and (XI). An example of the compound of formula (XI) is shown in formula (XIII) below.

Z is an electron-withdrawing group which may be absent in one or both occurrences. If Z is absent, $R^3$ and/or $R^4$ are directly bound to the carbon atom which in turn is directly bound to X or Y, respectively. Preference is given to one or two occurrences of Z being present within one group of formula (III).

Within the definition of $R^3$ and $R^4$ linear alkyl, alkenyl and alkinyl groups are preferred over branched alkyl, alkenyl and alkinyl groups. Furthermore, unsubstituted groups $R^3$ and $R^4$ are preferred. The term "substituted" refers to the presence of substituents, said substituents being selected from OH and halogen. Within alkyl, alkenyl and alkinyl, preference is given to alkyl. Preferred chain length of alkyl, alkenyl and alkinyl are $C_1$ to $C_6$, more preferred $C_1$ to $C_4$. Aryl preferably is a five- or six-membered ring. Preferred aryl groups include phenyl. As regards $H(OCH_2CH_2)_k$— and $H(OCH_2CH_2)_kO$—, preference is given to the following values of k: 1, 2, 3, 4 and 5. Particularly preferred values of k are 3 and 5.

In preferred embodiments, $R^3$ and $R^4$, independently for each occurrence, are selected from hydrogen, methyl, ethyl, n-propyl, i-propyl and $(H(OCH_2CH_2)_5$—$)$. Particularly preferred is that $R^3$ and/or $R^4$ is ethyl.

If Z is present, $H(OCH_2CH_2)_k$— is the preferred option of $H(OCH_2CH_2)_k$— and $H(OCH_2CH_2)O$—. It is understood that the crown ethers of the invention do not comprise peroxide groups. If Z is absent, $H(OCH_2CH_2)_kO$— is the preferred option of $H(OCH_2CH_2)_k$— and $H(OCH_2CH_2)_kO$—.

The crown ethers of formula (II) exhibit ether functional groups and at least one orthoester functional group. Lone electron pairs of the oxygens are available for forming a complex with a ligand. The envisaged ligands are detailed further below. Of particular relevance for complexation are ether oxygens which do not have an electron-withdrawing group (such as a carbonyl group) in their immediate vicinity. In this respect, the cyclic compounds of the invention resemble crown ethers of the prior art (see above). Crown ethers of the prior art, in particular those in which ether groups are the only oxygen-containing functional groups, while suitable for complexation, however, have the disadvantage that they are not biodegradable or not biodegradable to a sufficient extent.

Regarding the orthoester functional group(s), we note that orthoesters are amenable to hydrolysis in organisms and accordingly biodegradable. Elimination (also referred to as "clearance") of the orthoester is further facilitated in presence of one or two electron-withdrawing groups (designated "Z"). Particularly preferred Z groups are esters, which upon hydrolysis yield groups which are negatively charged at physiological pH, thus permitting more rapid elimination of the orthoester. To explain further, two ester groups (with the carbonyl group of the ester group being directly bound to the cyclic structure indicated in formula (III)) generate two negatively charged carboxylates, thereby further facilitating elimination. Degradation of the crown ether according to the invention may yet be further facilitated by the presence of one or more oxo groups as defined above.

As such, the crown ethers according to the invention provide an advantageous compromise between complexation capability and biodegradability as conferred by one or more orthoester functional groups.

Accordingly, the compounds according to the invention are biodegradable and biocompatible. The term "biodegradable" refers to substances which are degradable in living organisms. The term "biocompatible" denotes substances which do not give rise to adverse reactions of the human or animal body, preferably neither in their intact form nor when degraded. The term "biocompatible" is equivalent to "generally recognized as safe (GRAS)". Means for assessing biocompatibility are well known in the art, include in vitro tests performed on cell lines, in vivo tests on animals as well as clinical tests on human beings and do not have to be further detailed here. Any test required or recommended by regulatory authorities for the assessment of whether a compound is generally recognized as safe (GRAS), is preferably employed.

Biodegradability may be expressed in quantitative terms for example in terms of the half-life of a crown ether of the invention in plasma. Means and methods for determining half-life in plasma are known in the art. For example, a crown ether is mixed with plasma from a plasma pool and subsequently incubated at 37° C. while agitating. At given timepoints, aliquots are removed and analyzed by HPLC.

The term "half-life" refers to period of time required for the opening of the ring structure of formula (II). Typically, the following series of reactions occurs in plasma or under physiological conditions. First, hydrolysable groups Z such as ester groups are hydrolyzed if present. If the carbonyl group of the ester group is directly bound to the cyclic structure of formula (III), hydrolysis generates a carboxylate attached to the orthoester. Subsequently, and facilitated by the carboxylate, the orthoester is eliminated. As a consequence, the ring structure of formula (II) opens. If Z is absent in all occurrences, the orthoester elimination will generally be the first reaction to occur (in that case without facilitation by a electron-withdrawing group). In either case, the opening of the ring is the event which is determined when determining half-life in plasma or under physiological conditions. Accordingly, biodegradability refers to the capability of the ring to open in a biological environment, more specifically in plasma or under physiological conditions. Examples of physiological conditions are given below.

Upon opening of the ring, further reactions, leading to further degradation will follow. If more than one orthoester is present, and all orthoesters have the same structure, it is expected that elimination of the remaining orthoesters will rapidly follow the elimination of the first orthoester. In case the orthoesters are different in structure, the elimination of the more stable orthoesters, for example those with only one or no group Z present, will occur in a delayed manner on average. If only one orthoester is present, further degradation may be facilitated by the presence of one or more oxo groups as defined above. According to a preferred embodiment, the carbon atom bearing the oxo group is directly adjacent to an ether oxygen of the ring structure of the crown ether, thereby giving rise to an ether group. Such an ester group is hydrolysable in plasma and under physiological conditions.

In a preferred embodiment, the half-life of a crown ether of the invention in plasma is shorter than 24 hours, more preferably shorter than 12 hours, 6 hours, 3 hours, 2 hours, 1 hour, 30 min, 20 min, 10 min or 5 min. The term "biodegradable" refers to degradation of said crown ether, wherein it is understood that degradation consists of or includes cleavage or hydrolysis of a least one orthoester group of said crown ether.

The terms "complex" and "complexation" are well known in the art and refer to a reversible association of molecules, atoms, or ions through non-covalent chemical bonds. Usually two interaction partners, a complexing agent having a plurality of functional groups and a small molecule, atom or ion bound by said plurality of functional groups are implied. As used herein, the term complex is not confined to metal ions bound to a complexing agent. It relates in general to complexes between a compound of the invention and a cation or cationic group also referred to as ligand. The crown ethers of the invention provide oxygen-containing functional groups, the oxygen being available for complex formation.

The crown ethers according to the invention have the further advantage that their interaction (complex formation) with an active agent (further detailed below) is transient. The term "transient" as used herein refers to reversibility under physiological conditions. Upon passage of the cell membrane, mucosa and/or skin, the cyclic compounds either detach from the active agent, for example as a consequence of the presence of competing ligands such as ammonium ions or primary or secondary amides, and/or they are degraded.

In a preferred embodiment, at least one occurrence in the crown ether of $R^1$ and $R^2$ together form an oxo group.

It is understood that (i) no acid anhydride is present in those cases where more than one oxo group is present, and (ii) an oxo group and a group of formula (III) are not present at the two positions adjacent to the same ether oxygen, noting that in such a case an anhydride would be formed upon hydrolysis of the orthoester comprising the group of formula (III).

In a further preferred embodiment, the ring structure of said crown ether is provided by 18-crown-6,12-crown-4,13-crown-4,14-crown-4,15-crown-5,16-crown-5,17-crown-5, 20-crown-6,21-crown-7 or 24-crown-8. Particularly preferred is 18-crown-6.

In a further preferred embodiment, one or two oxo groups are present.

It is preferred that the carbon atom bearing the oxo group is directly adjacent to an ether oxygen atom of the ring structure of said crown ether, thereby given rise to an ester group.

In a further preferred embodiment, the number of ether oxygen atoms in the ring is an even number and one oxo group is present adjacent to every other ether oxygen atom.

In a further preferred embodiment, (a) one group of formula (III) and two oxo groups; (b) two groups of formula (III) and one oxo group; or (c) three groups of formula (III) and no oxo group are present. In a particularly preferred embodiment, the ring structure of said crown ether is provided by 18-crown-6 and the three groups according to any of options (a) to (c) are located on every other building block, said building block being the group in square brackets of formula (II) above. More preferably, the three groups according to any of options (a) to (c) are located such that a three-fold symmetry is present. An example of three-fold symmetry is shown below.

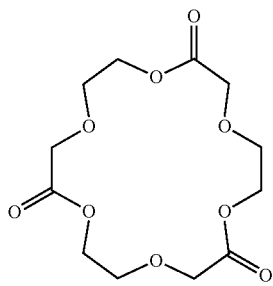 [SMILES: O=C1COCCOC(=O)COCCOC(=O)COCCO1]

According to the embodiment described above, one, two or three of the displayed oxo groups are replaced with a group of formula (III).

In an alternative preferred embodiment, (a) one group of formula (III) and one oxo group are present, wherein the carbon atom of said group of formula (III), said carbon atom being part of the ring structure of the crown ether, is directly bound to the carbon atom bearing the oxo group; or (b) two groups of formula (III) are present, wherein the two carbon atoms of said two groups of formula (III), said carbon atoms being part of the ring structure of the crown ether, are directly bound to each other.

This embodiment includes embodiments, wherein the crown ether can be seen to comprise an oxalic acid moiety, wherein both carboxyl groups of said oxalic acid moiety are involved in ester bonds within the crown ether ring, and furthermore one or two of said ester bonds is modified to be an orthoester. Particularly preferred crown ethers of this type are the crown ethers of formulae (VI) to (VIII).

In a further preferred embodiment, L is a covalent bond.

In a further preferred embodiment, both X and Y are O.

In a preferred embodiment, Z is selected from —O—C(=O)—, —C(=O—O— and —C(=O)—. Particularly preferred is that $R^3Z$ and/or $R^4Z$ are $R^3$—O—C(=O)— and/or $R^4$—O—C(=O)—.

In a further preferred embodiment, $R^3$ and $R^4$ are independently selected from hydrogen, methyl, ethyl, n-propyl, i-propyl, 2,3-dihydroxy-propyl, and $H(OCH_2CH_2)_5$—. In a more preferred embodiment, $R^3$ and $R^4$ are selected to be the same.

In a further preferred embodiment, $R^3$—Z and independently $R^4$—Z are selected from ethyl-oxy-carbonyl, 2,3-dihydroxy-propyl-oxy-carbonyl, and $H(OCH_2CH_2)_5$—O—C(=O)—. Preferably, $R^3$—Z and $R^4$—Z are the same. Particularly preferred is that $R^3$—Z and/or $R^4$—Z is/are ethyl-oxy-carbonyl.

Particularly preferred crown ethers of the invention are shown below,

Formula (IV)

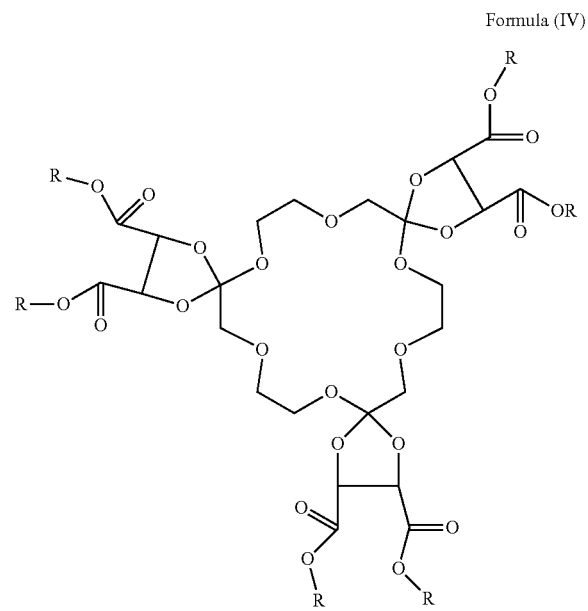

Formula (V)
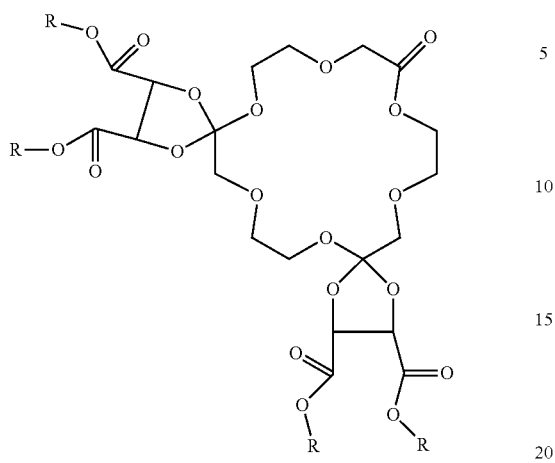
Formula (VI)
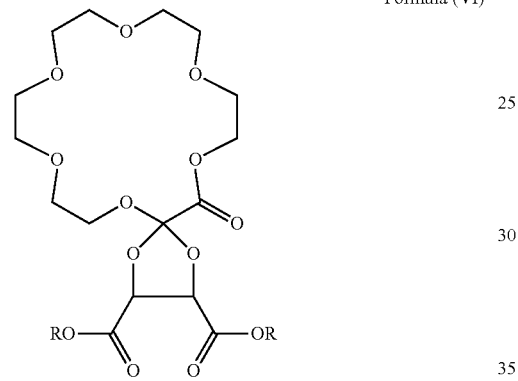
Formula (VII)
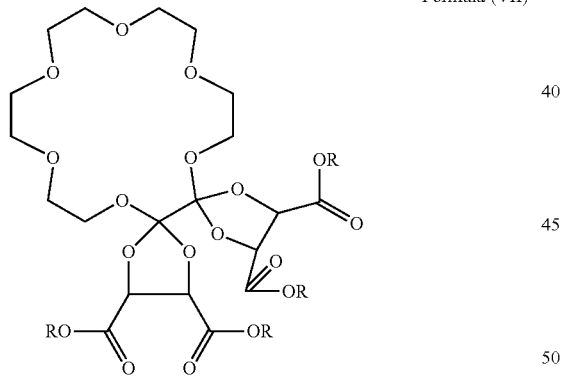
Formula (VIII)
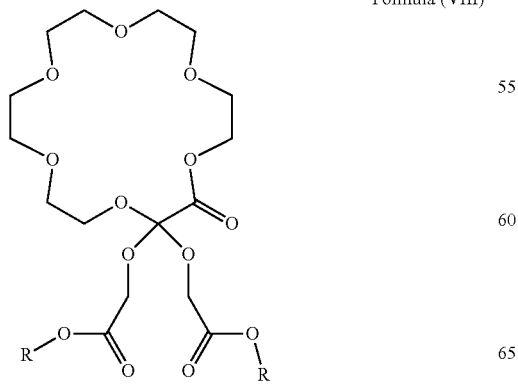
Formula (IX)
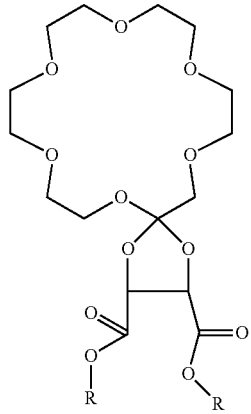
Formula (X)
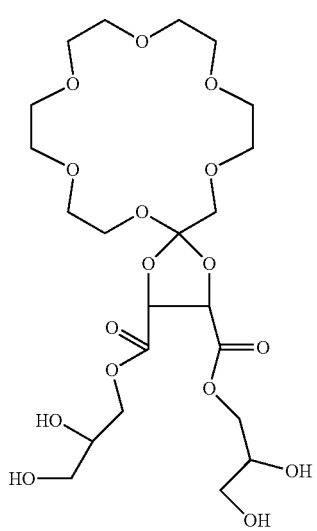
Formula (XI)
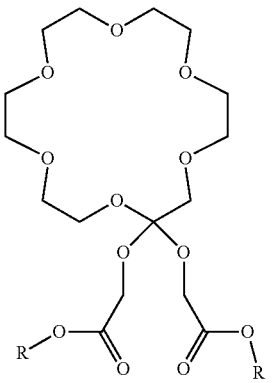

Formula (XII)

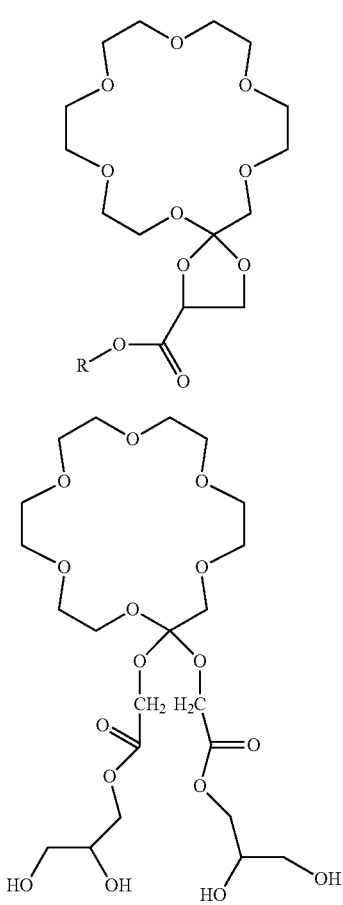

Formula (XIII)

wherein R, independently for each occurrence, is selected from hydrogen; linear or branched and substituted or unsubstituted $C_1$ to $C_{10}$ alkyl, alkenyl and alkinyl; substituted or unsubstituted aryl with up to 10 ring atoms; and $H(OCH_2CH_2)_k$—, wherein k is an integer number from 1 to 10; wherein substituents, if present, are selected from OH and halogen.

In preferred embodiments, R, independently for each occurrence, is selected from hydrogen, methyl, ethyl, n-propyl, i-propyl and $(H(OCH_2CH_2)_5$—). Particularly preferred is that R is ethyl.

Furthermore it is preferred that in embodiments with more than one occurrence of R, all occurrences of R are selected to be the same.

In case of formula (VIII), a particularly preferred group R is ethyl.

In a preferred embodiment of the composition according to the first aspect or the pharmaceutical or diagnostic composition according to the second aspect of the invention, said cyclic compound accounts for 0.1 to 60% w/w, preferably 0.3 to 30% w/w, and more preferably for 0.5 to 15% w/w of said pharmaceutical or diagnostic composition.

In a preferred embodiment of the pharmaceutical or diagnostic composition according to the invention, component (c) on the one hand and a mixture of components (a) and (b), preferably in relative amounts as comprised in said pharmaceutical or diagnostic composition, on the other hand differ in their log P values. Preferably, the difference in log P is between 2 and 10, more preferred between 3 and 8.

The log P value is a parameter commonly used to quantify hydrophobicity.

The mass flux of a molecule at the interface of two immiscible or substantially immiscible solvents is governed by its lipophilicity. The more lipophilic a molecule is, the more soluble it is in the lipophilic organic phase. The partition coefficient of a molecule that is observed between water and n-octanol has been adopted as the standard measure of lipophilicity. The partition coefficient P of a species A is defined as the ratio $P=[A]_{n\text{-}octanol}/[A]_{water}$. A figure commonly reported is the log P value, which is the logarithm of the partition coefficient. In case a molecule is ionizable, a plurality of distinct microspecies (ionized and not ionized forms of the molecule) will in principle be present in both phases. The quantity describing the overall lipophilicity of an ionizable species is the distribution coefficient D, defined as the ratio D=[sum of the concentrations of all microspecies]$_{n\text{-}octane}$/[sum of the concentrations of all microspecies]$_{water}$. Analogous to log P, frequently the logarithm of the distribution coefficient, log D, is reported.

If the lipophilic character of a substituent on a first molecule is to be assessed and/or to be determined quantitatively, one may assess a second molecule corresponding to that substituent, wherein said second molecule is obtained, for example, by breaking the bond connecting said substituent to the remainder of the first molecule and connecting (the) free valence(s) obtained thereby to hydrogen(s).

Alternatively, the contribution of the substituent to the log P of a molecule may be determined. The contribution $\pi_x$ of a substituent X to the log P of a molecule R—X is defined as $\pi_x=\log P_{R\text{-}X}-\log P_{R\text{-}H}$, wherein R—H is the unsubstituted parent compound.

Values of P and D greater than one as well as log P, log D and $\pi_x$ values greater than zero indicate lipophilic/hydrophobic character, whereas values of P and D smaller than one as well as log P, log D and $\pi_x$ values smaller than zero indicate hydrophilic character of the respective molecules or substituents.

The above described parameters characterizing the lipophilicity of the lipophilic group according to the invention can be determined by experimental means and/or predicted by computational methods known in the art (see for example Sangster, Octanol-water Partition Coefficients: fundamentals and physical chemistry, John Wiley & Sons, Chichester. (1997)).

In practice, log P, log D and $\pi_x$ values will vary to a certain extent according to the specific conditions under which they are measured.

It has been shown that for drugs or active agents (especially for small molecules) to have a reasonable probability of being well absorbed their log P value must not be greater than 5. The probability density of log P values of drugs on the market (see, for example, http://www.organic-chemistry.org/prog/peo/cLogP.html) shows a maximum at a log P value around 3.

In a preferred aspect of the pharmaceutical or diagnostic composition, said pharmaceutically active agent is exendin-4, parathyroid hormone (PTH), calcitonin (preferred salmon calcitonin), desmopressin and/or insulin]

In a third aspect, the present invention relates to a method of preparing a pharmaceutical or diagnostic composition according to the invention, said method comprising the following steps: (a) dissolving or homogeneously suspending a pharmaceutically or diagnostically active agent in component (c) as defined above; (b) mixing components (a) and (b) according to the invention; and (c) adding the mixture obtained in step (b) to the solution or suspension obtained in step (a); wherein steps (a) and (b) can be effected simultaneously or in any order.

This embodiment relates to the preparation of a pharmaceutical or diagnostic composition, said pharmaceutical or diagnostic composition preferably being characterized in that it has an enhanced capability of crossing cell membranes and/or crossing mucosa. The manufacture of pharmaceutical or diagnostic compositions according to the invention provides for the combining of two pre-mixed compositions. One composition is obtained in step (a) of the method of preparing a pharmaceutical or diagnostic composition according to the invention, which step yields a solution or suspension of the active agent in component (c), wherein, as further detailed herein above, said component may consist of one or more organic solvents, and may optionally comprise one or more cyclic compounds such as crown ethers as well as further optional constituents, such further constituent(s) being, for example, (an) antioxidant(s) such as N-acetyl-methionine (see also the section "step 4" of Example 1). Optional further constituents may also be Cremophor, preferably selected from Cremophor EL (polyethoxylated castor oil), Cremophor RH40 (PEG 40 hydrogenated castor oil) and Cremophor RH60.

The second pre-mixed composition is obtained by mixing components (a) and (b) as defined herein above, i.e. by mixing at least one mono-alkanoyl glycerol ester with at least one compound selected from the group consisting of cholesterol, phosphatidyl cholines and phosphatidyl glycerols, the acyl moieties thereof being as defined above in relation to component (a) and (b), respectively. Step (c) of the method of preparing a pharmaceutical or diagnostic composition provides for the combining of the two premixed compositions, thereby yielding the pharmaceutical or diagnostic composition according to the invention. As stated above, said pharmaceutically or diagnostically active agent is preferably a peptide, polypeptide, nucleic acid or small organic molecule; particularly preferred is a peptide or polypeptide.

Each of components (a) and (b), to the extent they comprise more than one compound, may be prepared in pre-mixed form as well. To this effect, the constituents of each component are mixed and preferably heated, preferably to a temperature between 40 and 70, more preferred between 50 and 60, and particularly preferred to 56° C. Reference is made to step 4 as described in Example I. The procedures described therein are generally applicable, either individually or in conjunction, for the purposes of the present invention.

In a preferred embodiment of the third aspect of the invention, said pharmaceutically or diagnostically active agent is peptide or polypeptide. In preferred embodiments, said peptide or polypeptide is lyophilized.

In other words, lyophilization of said peptide or polypeptide preferably precedes step (a) of the method according to the second aspect of the present invention. Preferably, said lyophilization yields said peptide or polypeptide in a highly charged state where the peptide or polypeptide is (i) stable and (ii) ionized to a significant degree. Accordingly, lyophilization preferably takes place at a pH which is far from the isoelectric point pI of said peptide or polypeptide. Typically, this is achieved by lyophilization under acid or mildly basic conditions (preferably at a pH between 2 and 8, more preferably between 4 and 7) and/or in the presence of counter ions such as salicylic acid. Sometimes sugars like sucrose, mannitol and/or other sugars and/or polyols can be added in the lyophilisation step.

In an alternative approach, the peptide with the acetate counter ion (or in the acetate form) is first dissolved in an aqueous solution of an acid, said acid being a stronger acid than acetic acid. Thereby, any counter ions present on the amino groups of said peptide or polypeptide are exchanged, the consequence being that said amino groups bear the anion of said acid as counter ion. Subsequently, the pH can be brought to neutrality, i.e. about pH=7, and then lyophilization is performed.

Furthermore, each of the procedures described in Example 1 may independently or in conjunction applied for processing a peptide or polypeptide active agent and preparing the composition according to the present invention.

Suitable acids in either approach, in addition to salicylic acid, are trifluoro acetic acid, tartaric acid, phosphoric acid, lactic acid, oxalic acid, fumaric acid, maleic acid, citric acid, alkyl sulfonic acids such as but not limited to methylsulfonic acid (methansulfonic acid), dodecyl sulfonic acid (laurylsulfonic acid), p-toluene sulfonic acid, dodecyl sulphate (lauryl-sulfate), an amino acid such as lysine, glycine, histidine, and arginine or a modified amino acid such as N-acetyl lysine amide, N-acetyl arginine amide and N-Acetyl Methionine, and N-Acetyl Taurine.

Generally, lyophilization is performed under conditions which retain a sufficient amount of water in association with the peptide or polypeptide, thereby maintaining salvation and stability of the peptide or polypeptide.

In a fourth aspect, the present invention provides a method of enhancing mucosal, dermal, transdermal, epithelial and/or transepithelial delivery of a pharmaceutically or diagnostically active agent.

The present invention provides means and methods for formulating pharmaceutically or diagnostically active agents, said agents preferably being peptides or polypeptides, and said formulations permitting or enhancing delivery across biological barriers, in particular mucosa. A particularly preferred mucosa is the oral mucosa. Other preferred mucosae are the mucosae of stomach, intestine, nose and lungs. In other words, while the art typically provides for delivery of peptide or polypeptide active agents by injection, the present invention provides a more convenient route of administration. The present inventors recognized that, by preparing a pharmaceutical or diagnostic composition according to the method of the third aspect of the invention, the mucosal, dermal, transdermal, epithelial and/or transepithelial delivery of the comprised pharmaceutically or diagnostically active agent is enhanced. Typically, it is enhanced to such an extent that the active agent, which previously has been considered as not being useful for oral delivery, can be orally delivered when formulated according to the present invention. The same considerations apply to the dermal, transdermal, epithelial and/or transepithelial delivery routes.

In a fifth aspect, the present invention provides the use of components (a), (b) and (c) as defined in the present specification in the preparation of a pharmaceutical or diagnostic composition.

Related to the fourth aspect, the present invention provides in a sixth aspect the use of components (a), (b) and (c) as defined in any one of claims 6 to 12 for enhancing mucosal, dermal, transdermal, epithelial and/or transepithelial delivery of a pharmaceutically or diagnostically active agent.

Preferably, and as stated above, said mucosal delivery is delivery across the oral mucosa.

In a seventh aspect, the present invention provides a kit comprising or consisting of components (a), (b), and optionally (c) as defined in the present specification.

As regards the embodiments characterized in this specification, in particular in the claims, it is intended that each embodiment mentioned in a dependent claim is combined with each embodiment of each claim (independent or dependent) said dependent claim depends from.

For example, in case of an independent claim reciting 3 alternatives A, B and C, a first dependent claim depending from the independent claim and reciting 3 alternatives D, E and F and a second dependent claim depending from the independent claim and the first dependent claim and reciting 3 alternatives G, H and I, it is to be understood that the specification unambiguously discloses embodiments corresponding to combinations A, D, G; A, D, H; A, D, I; A, F, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim, a first dependent claim back to depending from the independent claim, and a second dependent claim depending from both the first dependent claim and the independent claim, it follows that the combination of the subject-matter of second dependent claim and the independent claim is clearly and unambiguously disclosed as is the combination of the subject-matter of the independent claim and the first and second dependent claims. In case a third dependent claim is present which refers to any one of the independent claim and the first and second dependent claims, it follows that the combination of the subject-matter of the third dependent claim and the independent claim, of the third and first dependent claims and the independent claim, of the third and second dependent claims and the independent claim, as well as of all three dependent claims and the independent claim is clearly and unambiguously disclosed.

DETAILED DESCRIPTION OF THE INVENTION

Figure 1A:
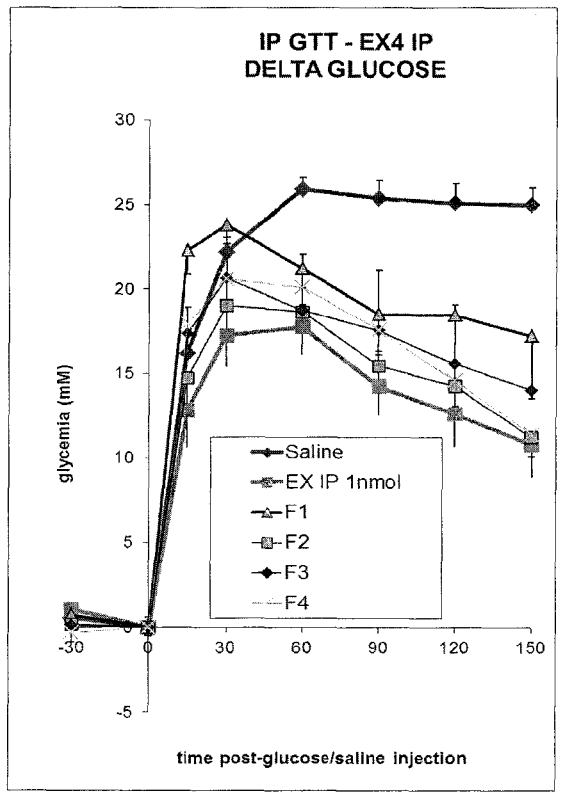
FIGS. 1a, 1b, 1c, 1d are plots of glycemia as a function of time.
Figure 1B:
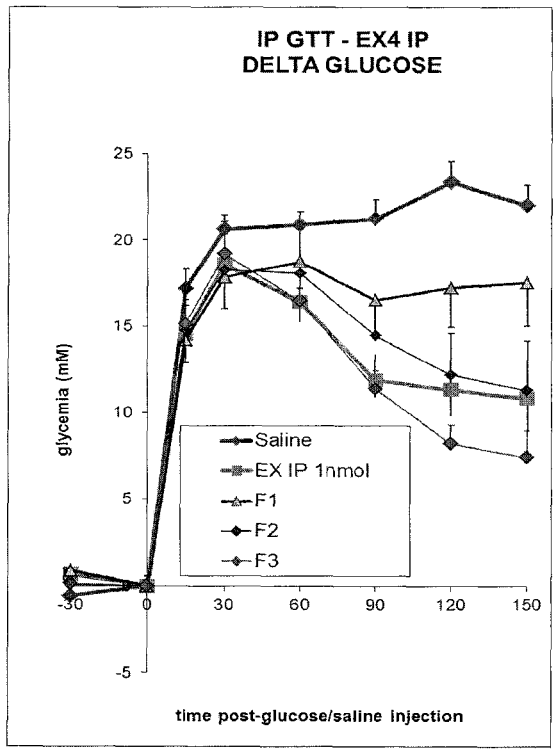
Figure 1C:
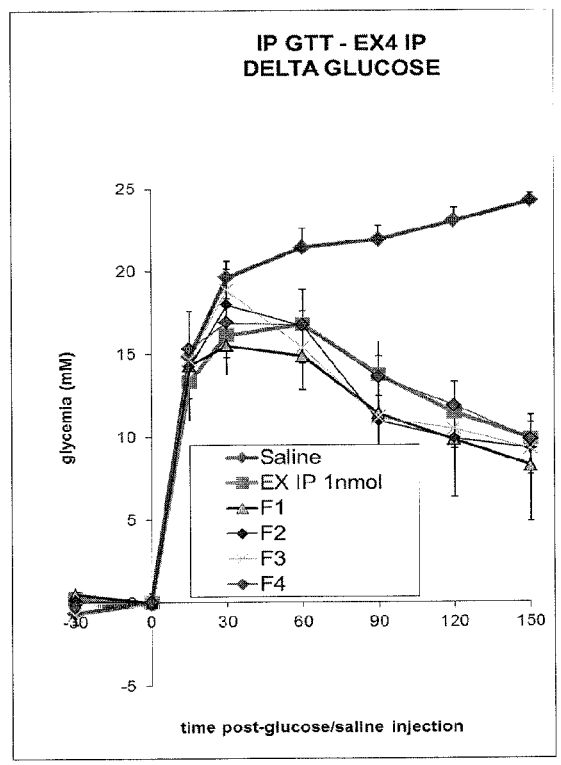
Figure 1D:
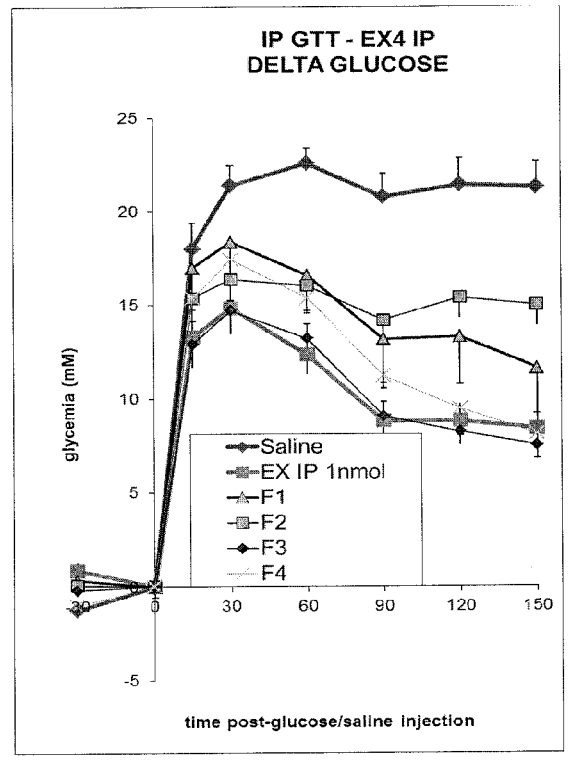

The figures show in detail:

FIGS. 1a, 1b, 1c, 1d: Glycemia (mM) as a function of time (minutes) upon exendin-4 IP injection or sublingual administration. All groups received NaCl 0.9% solution and a Glucose solution.

Group "saline": 5 mice treated only with the glucose solution

Group "IP": 5 mice injected IP (intraperitoneal) with 1 nmol exendin-4

Groups F1 to F4: 5 mice treated with formulations F1 to F4 (sublingual administration)

In all formulations, the peptide-crown ether complex in propylene glycol (12 equivalents crown ether, for example formula IX) was incorporated into compositions described below. The peptide crown complex was obtained by dissolving exendin-4 in a mixture of propylene glycol and crown ether. Typically, for a 1 mM final concentration of exendin-4 in formulation (2 µl administration, 2 nmol), 0.60 mg exendin-4 (120 nmol) were dissolved in a mixture of 0.67 mg crown structure (formula IX, 1440 nmol, 12 equivalents) and 14 µl propylene glycol. The obtained solution was finally combined with 106 µl of the compositions described below to yield 120 µl total volume of the pharmaceutical compositions according to the invention.

(a) 3 µl/mouse sublingual administration, containing 3.75 nmol exendin-4 (3.75 fold excess compared to IP).
F1=Composition Oleic; F2=Composition Lipoleic2; F3=Composition Lipoleic; F4=Composition Lipolinolein (b) 3 µl/mouse sublingual administration, containing 2.5 nmol exendin-4 (2.5 fold excess compared to IP).
F1=Composition Oleic; F2=Composition Lipoleic2; F3=Composition Lipoleic2 containing 10% crown ether (formula IX)

(c) 3 µl/mouse sublingual administration, containing 2.5 nmol exendin-4 (2.5 fold excess compared to IP).
F1=Composition Oleic containing 10% crown ether (formula IX); F2=Composition Lipoleic2 containing 10% crown ether (formula IX); F3=Composition Lipoleic3; F4=Composition Lipoleic2 containing 5% crown ether (formula IX)

(d) 2 µl/mouse sublingual administration, containing 2 nmol exendin-4 (2 fold excess compared to IP).
F1=Composition Oleic containing 10% crown ether (formula IX); F2=Composition Oleic containing 10% crown ether; F3=Composition Lipoleic3; F4=Composition Lipoleic6

Figure 2:
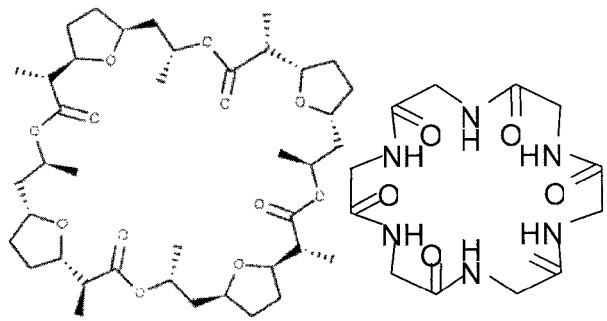
FIG. 2 shows examples of polyesters and polyamides.
Figure 2:
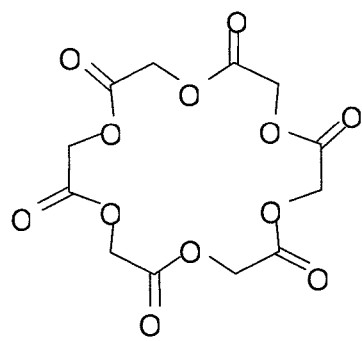
Figure 2:
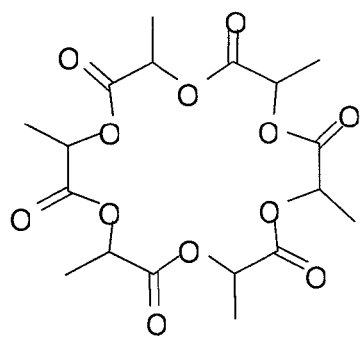
Figure 2:
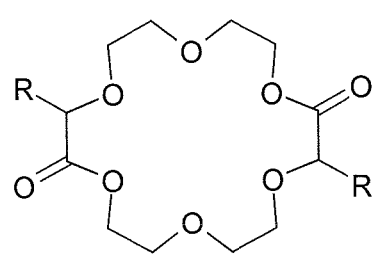
Figure 2:
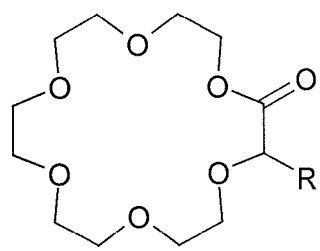

FIG. 2: Examples of polyesters and polyamides

The Examples illustrate the Invention.

Example 1

General Procedures for Preparation of Formulations

STEP 1: Alternative Peptide Solubility Improvement by Desalting

Peptides were optionally desalted by Reverse Phase High Performance Chromatography (RP-HPLC) (solvents were water and acetonitrile in the presence of 1% acetic acid) and lyophilized (i.e., freeze dried at less than room temperature). Depending on the pI of the molecule, the molecule is either utilized as it is in lyophilized form, or when required, re-dissolved or suspended in water or water/acetonitrile mixtures. The pH of the obtained solution or suspension was then brought to a desired value ranging from 4 to 7.5 such that the pH was sufficiently different from the pI of the molecule to insure solubility in various solvents employed in subsequent counter ion exchange and/or complexing reactions. When the desired pH was reached, the obtained solution or suspension was if necessary filtered through a 0.45 µm filter and lyophilized at this given pH ranging from 4 to 7.5. This treatment was found to be critical for further peptide solubility in various solvents or solvent mixtures (e.g., water/acetonitrile mixtures, organic solvents.)

STEP 2: Alternative Counter Ion Exchange

Peptide counter ion (usually acetate counter ion) was alternatively substituted by acidic compounds such as salicylic acid, different substituted or not benzoic acid derivatives, oxalic acid, sulfonates, sulfates such as lauryl sulfate, phosphatidylglycerol derivatives such as dilaurylphosphatidyl glycerol (DLPG), phosphoric acid, trifluoroacetic acid or chloride. This counter ion exchange was found to affect protein/peptide solubility and/or in vivo activity.

For example, the peptide acetate was converted to salicylate salt by the following treatment. To peptide acetate dissolved in water or ACN/H$_2$O 50/50 mixture was added a ACN/H$_2$O 50/50 solution of salicylic acid appropriate amount (138.12 g/mol). In some cases, mannitol (10-20% final concentration in the formulation mixture) and/or glycerol (1% final concentration in the formulation mixture) were added to the mixture. The obtained solution was then freeze-dried, affording peptide salicylate as a white solid.

STEP 3: Preparation of the Peptide-Crown Compound Complex

A solution of cyclic crown compound (appropriate amount of crown compound in a ratio of 1 to n equivalents regarding peptide/protein basic amino acid content) in an organic solvent (propylene glycol, NMP or a mixture) was added to the peptide salt. The obtained mixture was kept at room temperature (or if needed at 40° C.) till total dissolution occurred (typically 15-45 minutes), generating a limpid solution comprising the peptide salt-crown compound complex.

STEP 4: Final Formulation Preparation

A viscous non-aqueous hydrophobic formulation vehicle was added to peptide-crown compound complex and the resulting mixture, let at room temperature for 30 minutes then heated at 40° C. for 10 minutes. The obtained limpid preparation was then stored at +4° C.

Formulation 1:

The first part of the formulation vehicle was prepared by adding oleic acid (80 µl) and nonanoic acid (100 µl) to a mixture of octanoyl glycerol (130 mg) and decanoyl glycerol (130 mg). The obtained mixture was heated at 56° C. for complete dissolution. 200 µl of this latter were then added to a total 100 mg mixture (part 2) including 26.7 mg cholesterol, 7.2 mg DSPC and 66.3 mg DSPC. The obtained mixture was heated again at 56° C. till complete dissolution (2-8 hours), affording the viscous non-aqueous hydrophobic formulation vehicle. In the case of protein/peptide sequences including residues susceptible to oxidation, 0.25 mg N-acetyl-methionine (Ac-Met-OH) (191.25 g/mol) for 100 µl final formulation mixture may be added as anti-oxidizing agent and the mixture was heated again at 56° C. till a limpid solution was obtained.

Formulation 2:

The formulation vehicle was prepared by adding cyclic crown compound (typically 15 mg or 15 µl) to 135 µl formulation 1. The obtained mixture was heated at 56° C. till complete dissolution (2-8 hours), affording the viscous non-aqueous hydrophobic formulation vehicle. In the case of protein/peptide sequences including residues susceptible to oxidation, 0.25 mg N-acetyl-methionine (Ac-Met-OH) (191.25 g/mol) for 100 µl final formulation mixture may be added as anti-oxidizing agent and the mixture was heated again at 56° C. till a limpid solution was obtained.

For the above non-aqueous hydrophobic vehicles (i.e. Formulations 1 and 2), one or more components were eliminated or replaced by analogous compounds for other formulations. For example, monolinolein can be used instead of oleic and/or nonanoic acids.

Example 2

Exemplary Compositions

Components (a)
Component "Oleic":
520 mg DecanoylGlycerol (DG)
160 µl oleic acid
200 µl nonanoic acid
Component "Oleic2":
260 mg DG
260 mg OctanoylGlycerol (OG)
160 µl oleic acid
200 µl nonanoic acid
Component "Oleic3":
260 µl monolinolein
260 mg OctanoylGlycerol (OG)
160 µl oleic acid
200 µl nonanoic acid
Component "Monolinolein":
65 mg DG
65 mg OG
90 µl monolinolein
Component "Ricinoleic2":
130 mg DG
130 mg OG
80 µl ricinoleic acid
100 µl nonanoic acid
Component "Ricinolein2":
130 mg DG
130 mg OG
40 µl ricinoleic acid
50 µl nonanoic acid
90 mg monolein
Compositions (Above Components (a)+Components (b))
Composition "Lipoleic":
66.3 mg distearoyl phosphatidyl choline (DSPC)
7.2 mg distearoyl phosphatidyl glycerol (DSPG)
26.7 mg cholesterol
200 µl composition "oleic"
Composition "Lipoleic2":
198.9 mg DSPC
21.6 mg DSPG
80.1 mg cholesterol
600 µl component "oleic2"
Composition "Lipoleic3":
100 mg DSPC
200 µl component "oleic2"
Composition "Lipoleic6":
66.3 mg DSPC
7.2 mg DSPG
26.7 mg cholesterol
200 µl component "oleic3"
Composition "Lipolinolein":
66.3 mg DSPC
7.2 mg DSPG
26.7 mg cholesterol
200 µl component "monolinolein"
Composition "Liporicino":
75 mg DSPC
300 µl component "ricinoleic2"
Composition "Lipomix":
75 mg DSPC
300 µl component "ricinolein2"
Composition "Lipolysoricino":
75 mg MSPC (18:0 lyso PC)
300 µl component "ricinoleic2"

Composition "Liporicino-DLPC":
75 mg DLPC (12:0 PC)
300 µl component "ricinoleic2"

Example 3

Glycemia (mM) as a Function of Time (Minutes) Upon Exendin-4 IP Injection or Sublingual Administration All groups received NaCl 0.9% solution and a Glucose solution. Group "saline": 5 mice treated only with the glucose solution. Group "IP": 5 mice injected IP (intraperitoneal) with 1 nmol exendin-4. Groups F1 to F4: 5 mice treated with formulations F1 to F4 (sublingual administration). In all formulations, the peptide-crown ether complex in propylene glycol (12 equivalents crown ether, for example formula IX) was incorporated into compositions described below. The peptide crown complex was obtained by dissolving exendin-4 in a mixture of propylene glycol and crown ether. Typically, for a 1 mM final concentration of exendin-4 in formulation (2 µl administration, 2 nmol), 0.60 mg exendin-4 (120 nmol) were dissolved in a mixture of 0.67 mg crown structure (formula IX, 1440 nmol, 12 equivalents) and 14 µl propylene glycol. The obtained solution was finally combined with 106 µl of the compositions described in items (a) to (d) of the legend of FIG. 1.

Corresponding data are displayed in FIGS. 1a, 1b, 1c, and 1d.

The invention claimed is:

1. A pharmaceutical or diagnostic composition, comprising
    as a pharmaceutically or diagnostically active agent, a peptide, or polypeptide, and,
    as a delivery system for mucosal delivery of the pharmaceutically or diagnostically active agent, components (a) and (b) comprising
    (a) (i) at least one mono-alkanoyl glycerol ester, wherein alkanoyl is selected from $C_8$ to $C_{10}$ alkanoyl;
        (ii) an alkanoic acid selected from $C_2$ to $C_{21}$; and
    (b) (i) at least one compound selected from cholesterol, phosphatidyl cholines, lysophosphatidylcholines and phosphatidyl glycerols, wherein the acyl moieties of the phosphatidyl moieties are independently selected from $C_6$ to $C_{21}$ alkanoyl and $C_6$ to $C_{21}$ alkenoyl,
    and wherein the delivery system contains no water other than as an impurity.

2. The pharmaceutical or diagnostic composition according to claim 1, wherein said (a)(ii) alkanoic acid is selected from $C_6$ to $C_{12}$.

3. The pharmaceutical or diagnostic composition according to claim 1, wherein said (a)(ii) alkanoic acid is selected from $C_8$ to $C_{10}$.

4. A pharmaceutical or diagnostic composition, comprising
    as a pharmaceutically or diagnostically active agent, a peptide or polypeptide, and
    as a delivery system for mucosal delivery of the pharmaceutically or diagnostically active agent, as components (a) and (b) comprising
    (a) (i) at least one mono-alkanoyl glycerol ester, wherein alkanoyl is selected from $C_8$ to $C_{10}$ alkanoyl;
        (ii) an alkenoic acid selected from oleic, linoleic and elaidic acid; and
    (b) (i) at least one compound selected from cholesterol, phosphatidyl cholines, lysophosphatidylcholines and phosphatidyl glycerols, wherein the acyl moieties of the phosphatidyl moieties are independently selected from $C_6$ to $C_{21}$ alkanoyl and $C_6$ to $C_{21}$ alkenoyl,
    and wherein the delivery system contains no water other than as an impurity.

5. The composition according to claim 1, wherein component (a) comprises two mono-alkanoyl glycerol esters.

6. A pharmaceutical or diagnostic composition according to claim 1 or 4, further comprising, as a component (c)(i) a cyclic compound of formula (I), formula (I) being defined as follows

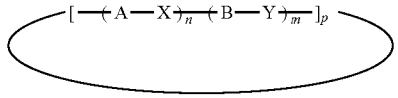

wherein
A, B independently in each occurrence is alkane-i,j-diyl having k carbon atoms, i and independently j being less than or equal k and k being selected from 1 to 10, wherein said alkane-i,j-diyl
    (1) may comprise one or more double bonds;
    (2) is optionally substituted; and/or
    (3) comprises a cycle, wherein the total number of cycles being cyclic sugars in said compound is selected from 0 to 4 and is less than $p \cdot (n+m)$;
X,Y independently in each occurrence is a biocompatible functional group comprising at least one oxygen atom or two sulfur atoms;
n, m independently of each other are selected from 0 to 20;
p is selected from 1 to 10;
n+m is equal or greater than 1; and
$p \cdot (n+m)$ is selected from 3 to 30;
wherein said cyclic compound is capable of forming a complex with a protonated primary amino group, a protonated secondary amino group, a protonated guanidinium group, and/or a metal ion.

7. The pharmaceutical or diagnostic composition according to claim 6, wherein component (c) has a log P value that differs from the log P value of a mixture of components (a) and (b).

8. The pharmaceutical or diagnostic composition according to claim 6, wherein said pharmaceutically active agent is exendin-4, parathyroid hormone, calcitonin, desmopressin and/or insulin.

9. The composition according to claim 5, wherein the two mono-alkanoyl glycerol esters are mono-octanoyl glycerol ester and mono-decanoyl glycerol ester.

10. A method of mucosal delivery to a human or other mammal of a pharmaceutically or diagnostically active agent, the method comprising orally administering the composition of claim 5 to the human or other mammal.

11. A method of mucosal delivery to a human or other mammal of a pharmaceutically or diagnostically active agent, the method comprising orally administering the composition of claim 6 to the human or other mammal.

12. A method of mucosal delivery to a human or other mammal of a pharmaceutically or diagnostically active agent, the method comprising orally administering the composition of claim 7 to the human or other mammal.

13. A method of mucosal delivery to a human or other mammal of a pharmaceutically or diagnostically active agent, the method comprising orally administering the composition of claim 8 to the human or other mammal.

14. A method of mucosal delivery to a human or other mammal of a pharmaceutically or diagnostically active agent, the method comprising orally administering the composition of claim 9 to the human or other mammal.

15. A method of mucosal delivery to a human or other mammal of a pharmaceutically or diagnostically active agent, the method comprising orally administering the composition of claim 1 to the human or other mammal.

16. A method of mucosal delivery to a human or other mammal of a pharmaceutically or diagnostically active agent, the method comprising orally administering the composition of claim 4 to the human or other mammal.

* * * * *